(12) United States Patent
Abrams

(10) Patent No.: US 7,997,265 B2
(45) Date of Patent: Aug. 16, 2011

(54) CRADLE FOR SEMI-AUTOMATIC EMERGENCY MEDICATION DOSE NEBULIZER

(76) Inventor: Robert Abrams, Oakdale, NY (US)

( * ) Notice: Subject to any disclaimer, the term of this patent is extended or adjusted under 35 U.S.C. 154(b) by 0 days.

(21) Appl. No.: 12/931,695

(22) Filed: Feb. 8, 2011

(65) Prior Publication Data

US 2011/0126826 A1 Jun. 2, 2011

Related U.S. Application Data

(63) Continuation of application No. 12/798,884, filed on Apr. 13, 2010, which is a continuation-in-part of application No. 12/380,135, filed on Feb. 24, 2009, which is a continuation-in-part of application No. 12/321,854, filed on Jan. 26, 2009, now Pat. No. 7,814,902, which is a continuation-in-part of application No. 12/283,303, filed on Sep. 11, 2008, now Pat. No. 7,784,459, which is a continuation-in-part of application No. 12/217,406, filed on Jul. 3, 2008, now Pat. No. 7,836,885, which is a continuation-in-part of application No. 11/901,628, filed on Sep. 18, 2007, now abandoned.

(51) Int. Cl.
*A61M 16/00* (2006.01)
*A61M 16/14* (2006.01)

(52) U.S. Cl. ......... 128/200.21; 128/200.14; 128/200.19; 128/202.27; 128/203.12; 128/203.19; 128/203.21; 128/207.14; 128/203.27; 239/338; 239/370

(58) Field of Classification Search ............. 128/200.21, 128/200.14, 200.19, 202.27, 203.12, 203.19, 128/203.21, 207.14, 203.27; 239/338, 370
See application file for complete search history.

(56) References Cited

U.S. PATENT DOCUMENTS

| | | | | | |
|---|---|---|---|---|---|
| 4,094,317 | A | * | 6/1978 | Wasnich | 128/200.16 |
| 5,551,416 | A | * | 9/1996 | Stimpson et al. | 128/200.16 |
| 2007/0265579 | A1 | * | 11/2007 | Kleyman et al. | 604/207 |
| 2008/0066747 | A1 | * | 3/2008 | Spink | 128/202.13 |

* cited by examiner

*Primary Examiner* — Justine R Yu
*Assistant Examiner* — Clinton Ostrup
(74) *Attorney, Agent, or Firm* — Alfred M. Walker

(57) ABSTRACT

A conventional respiratory nebulizer has an emergency medication dose storage system delivering the stored medication dose directly to the nebulizing chamber with a single impulse of manual force to a simple mechanical delivery system, To Compressor

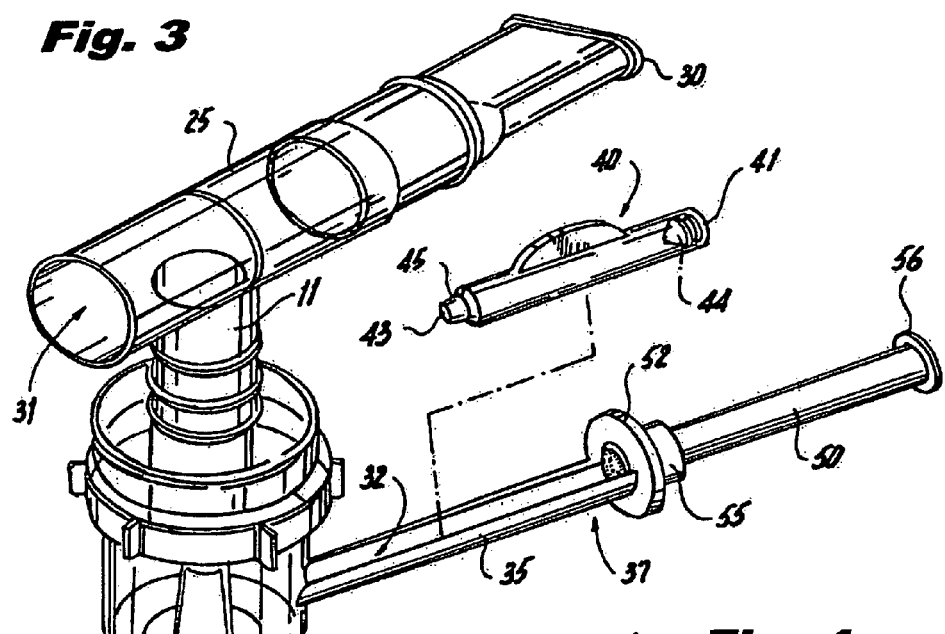
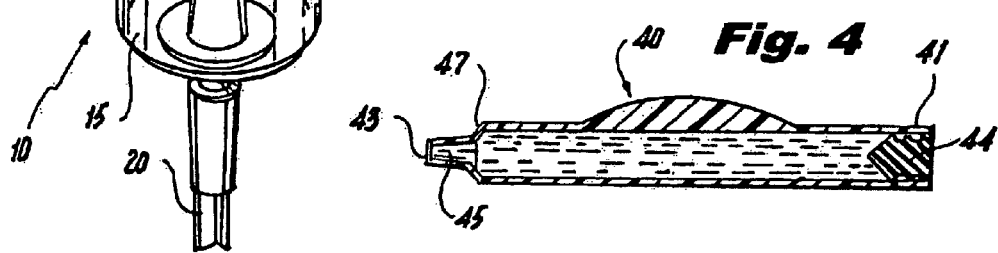
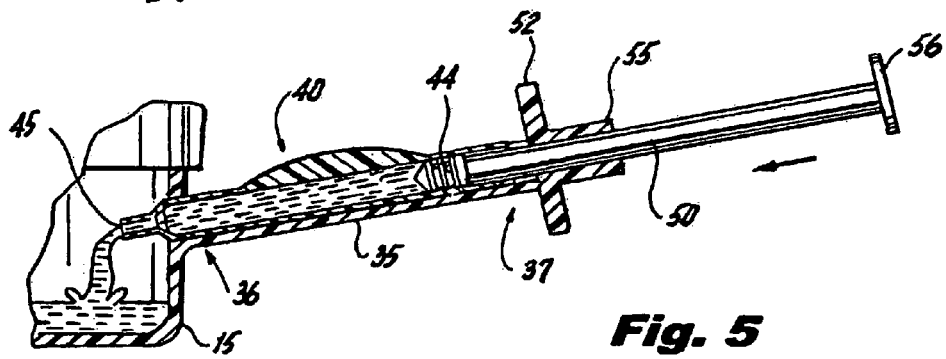

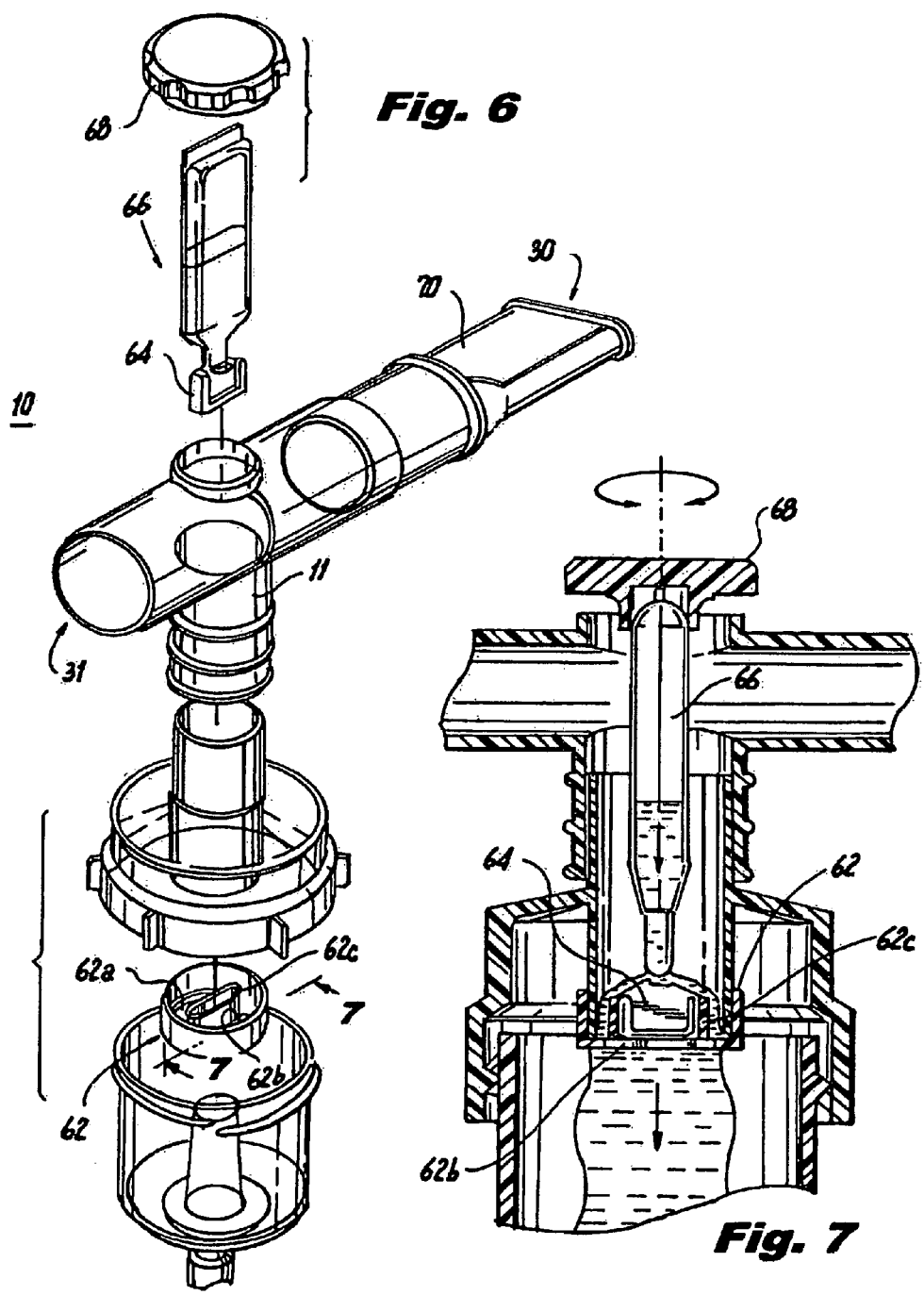

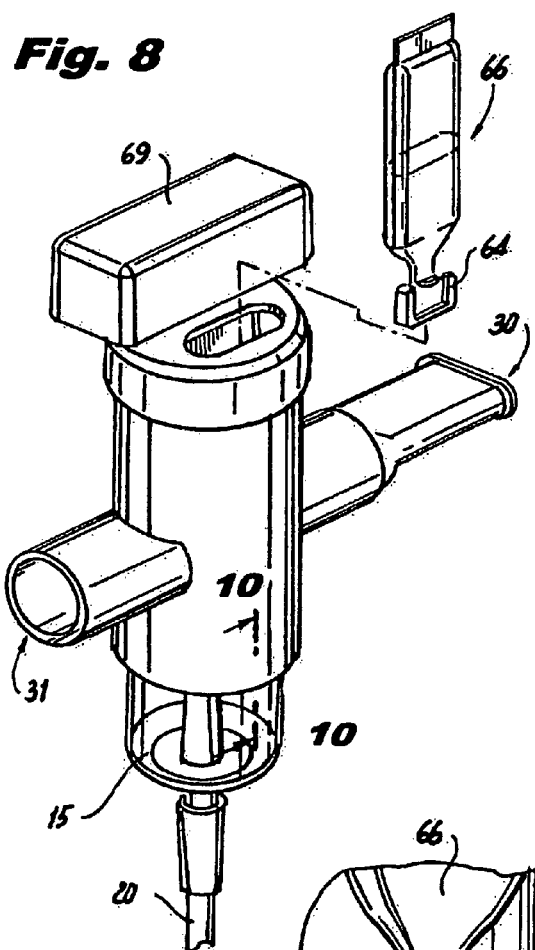
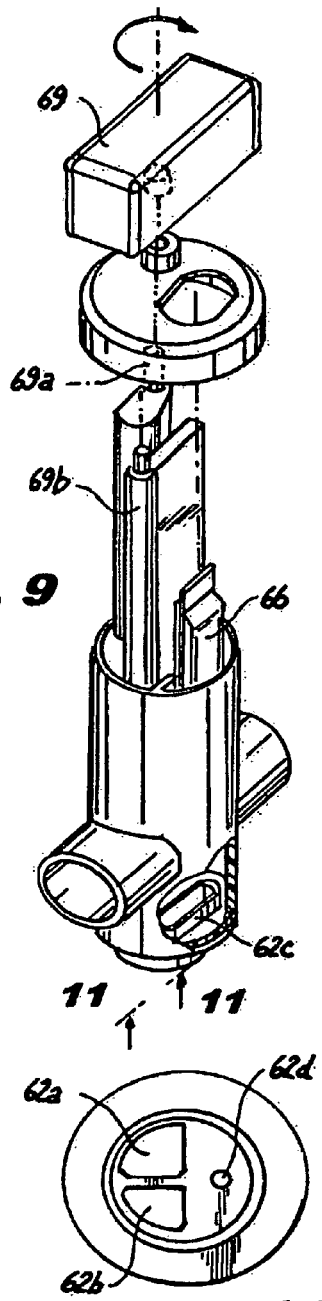
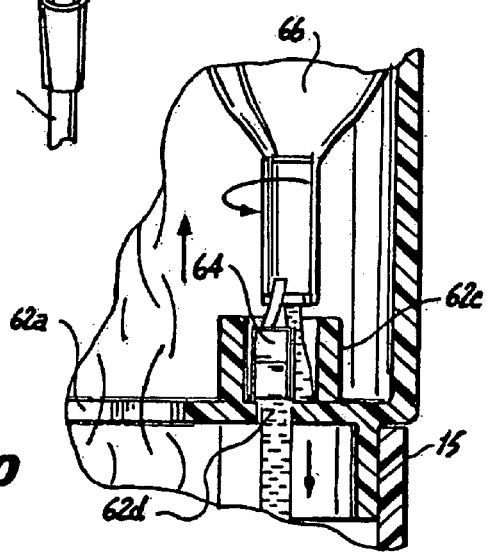
Fig. 8
Fig. 9
Fig. 10
Fig. 11

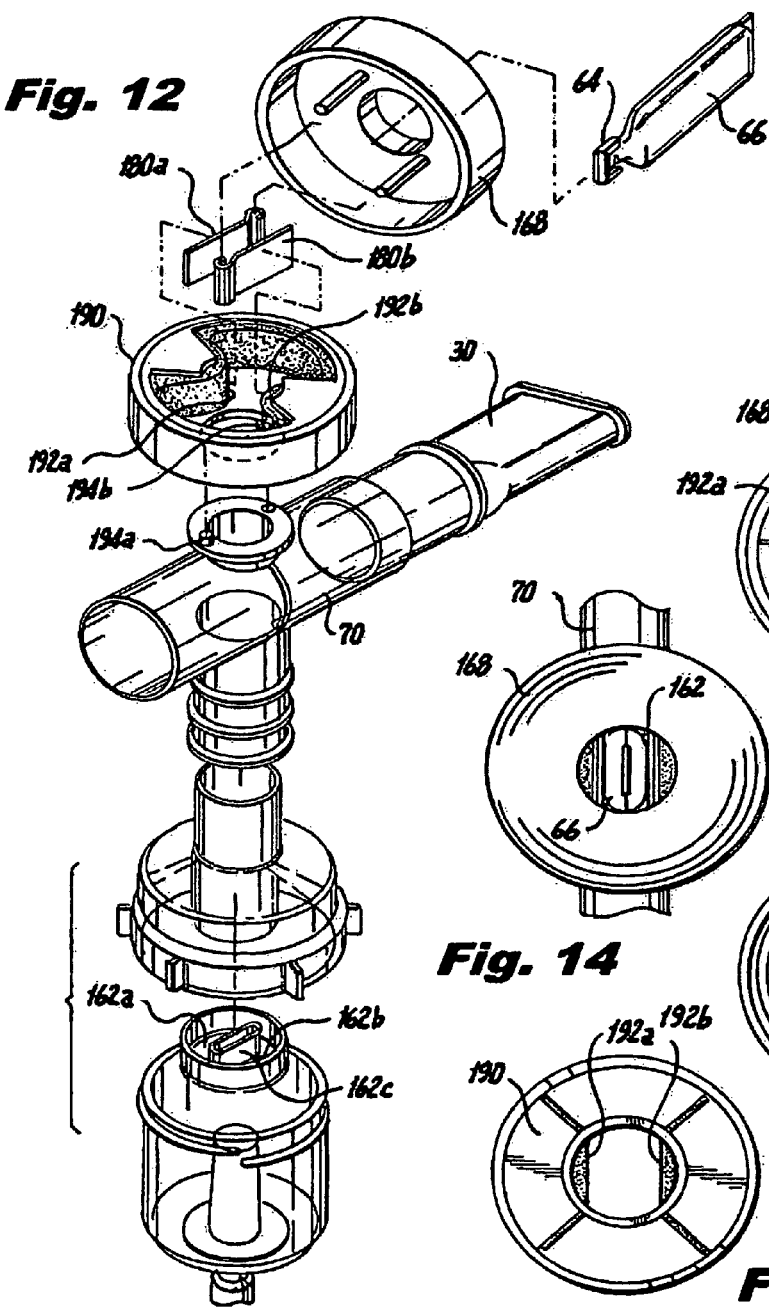

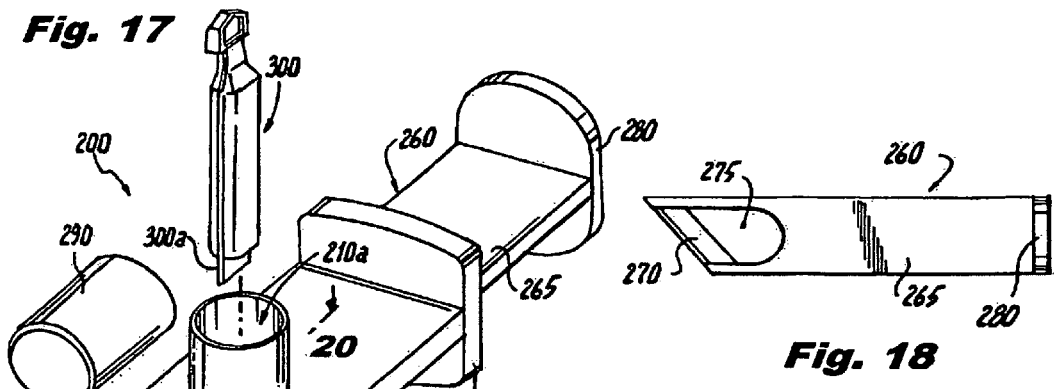
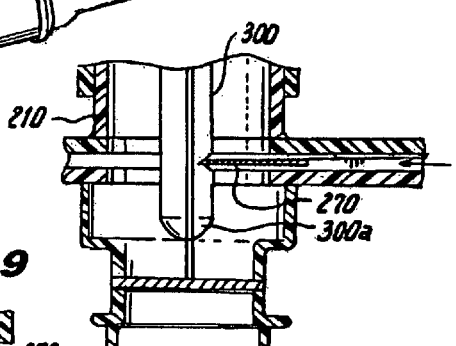
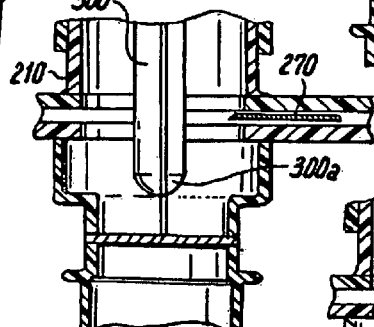
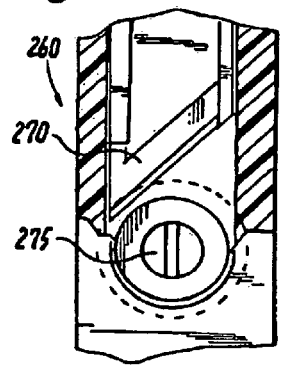
Fig. 17
Fig. 18
Fig. 19
Fig. 20
Fig. 21
Fig. 22

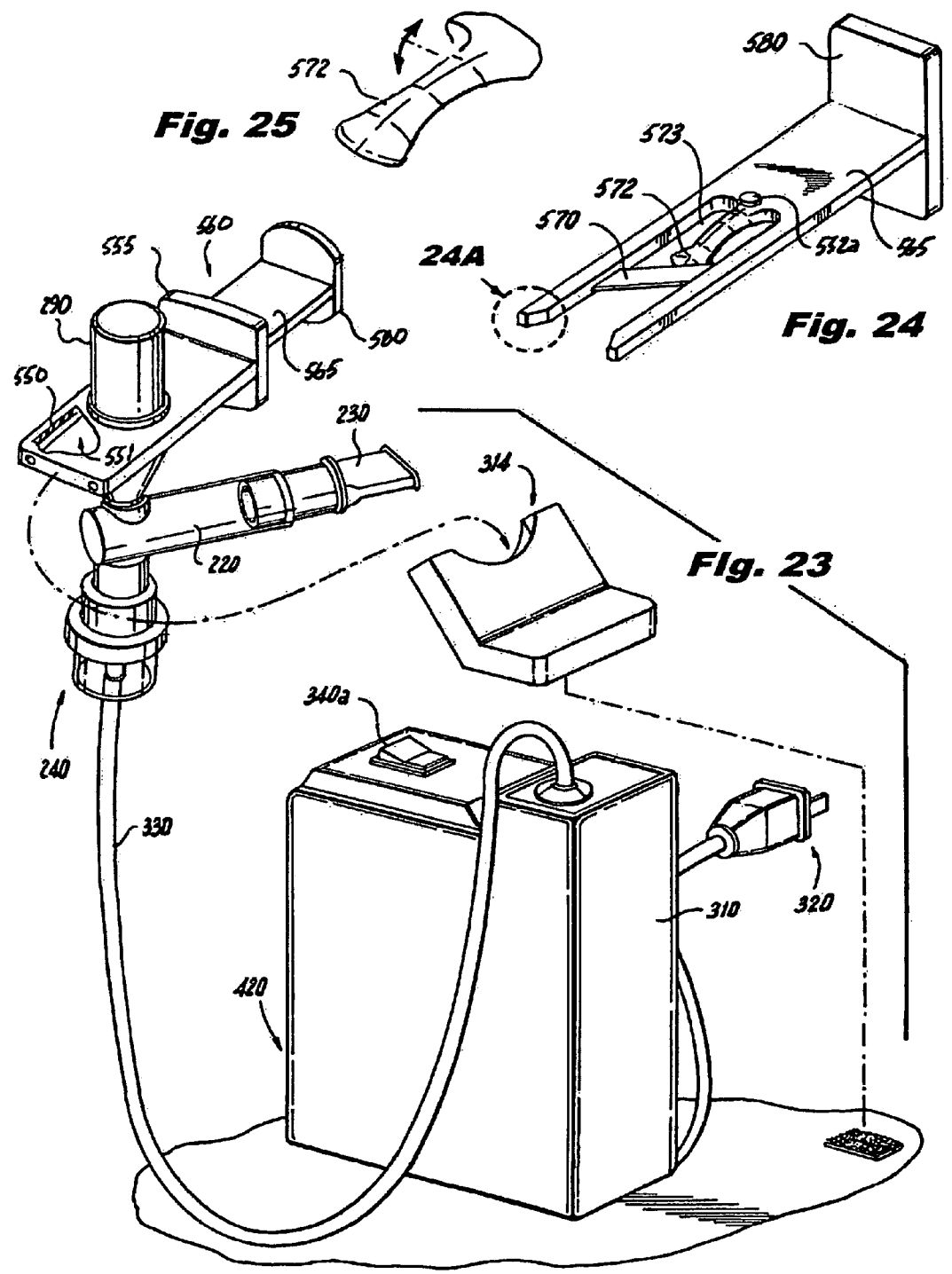

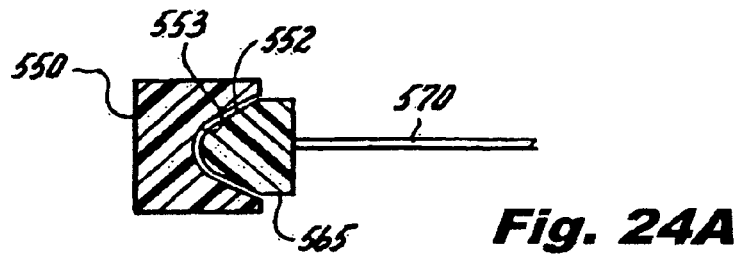
Fig. 24A
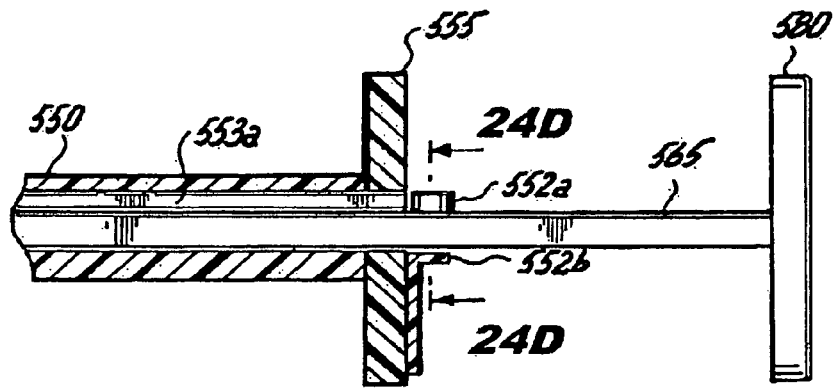
Fig. 24B
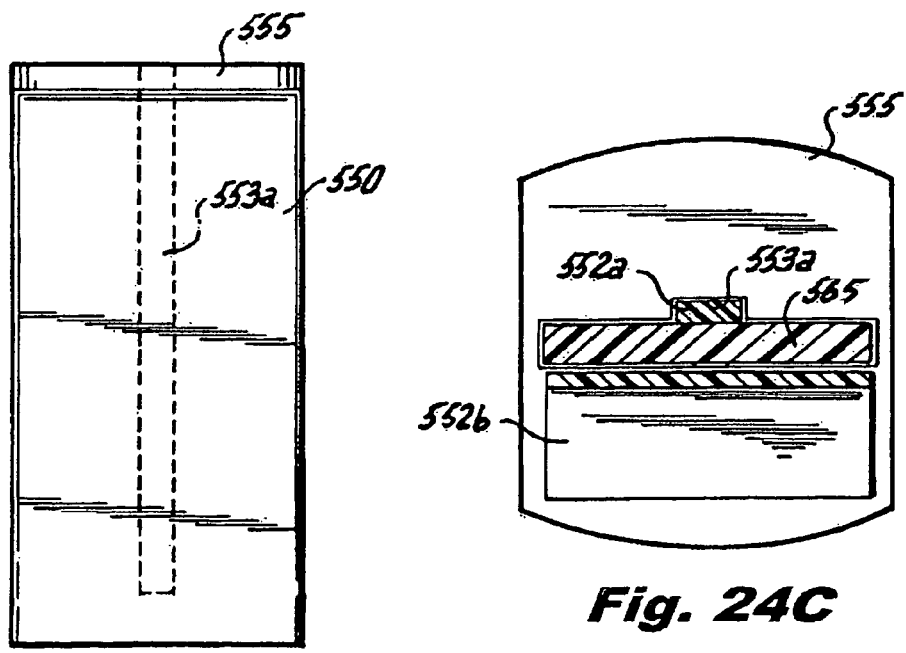
Fig. 24C
Fig. 24D

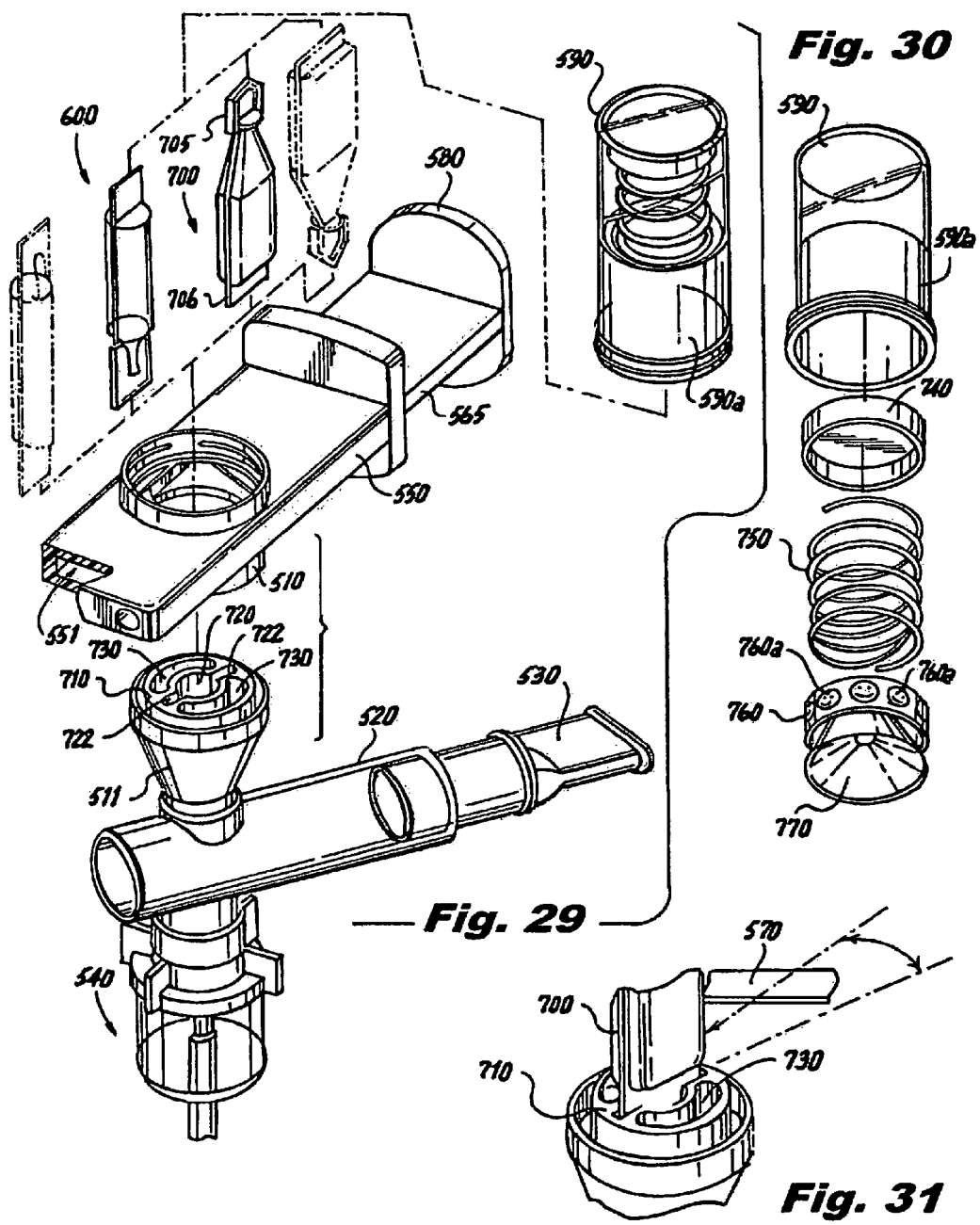

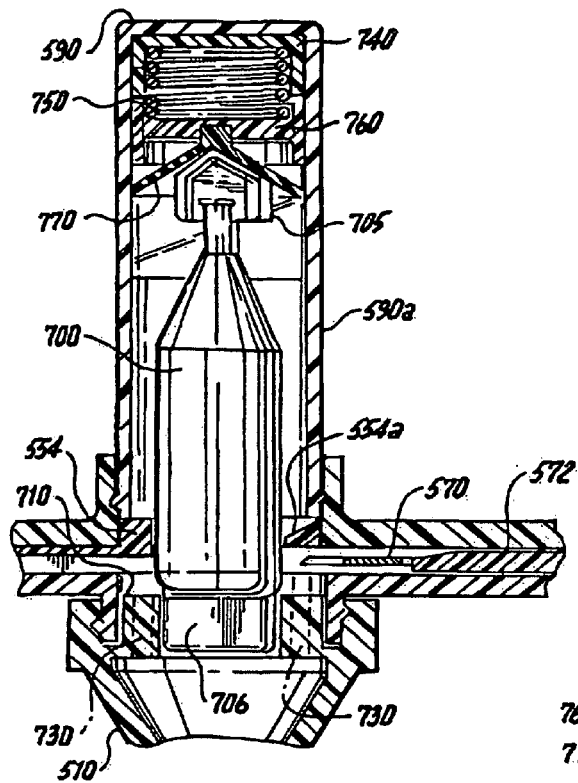
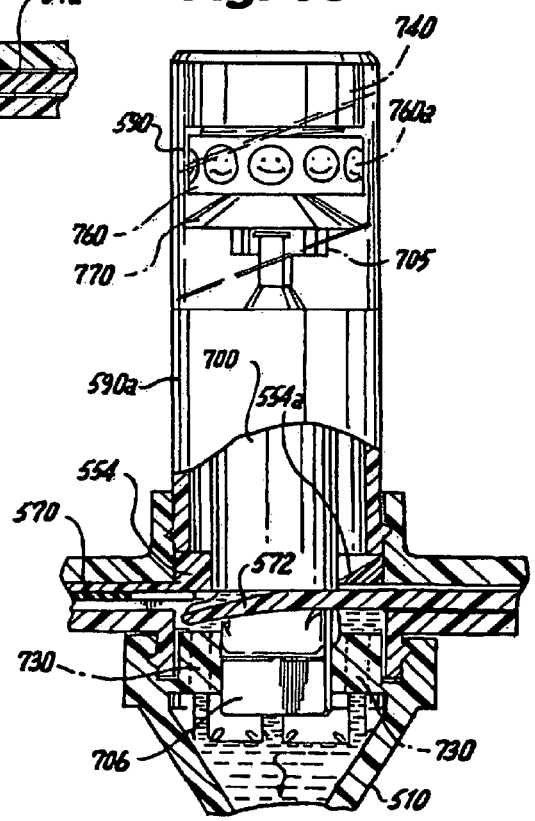
Fig. 32
Fig. 33

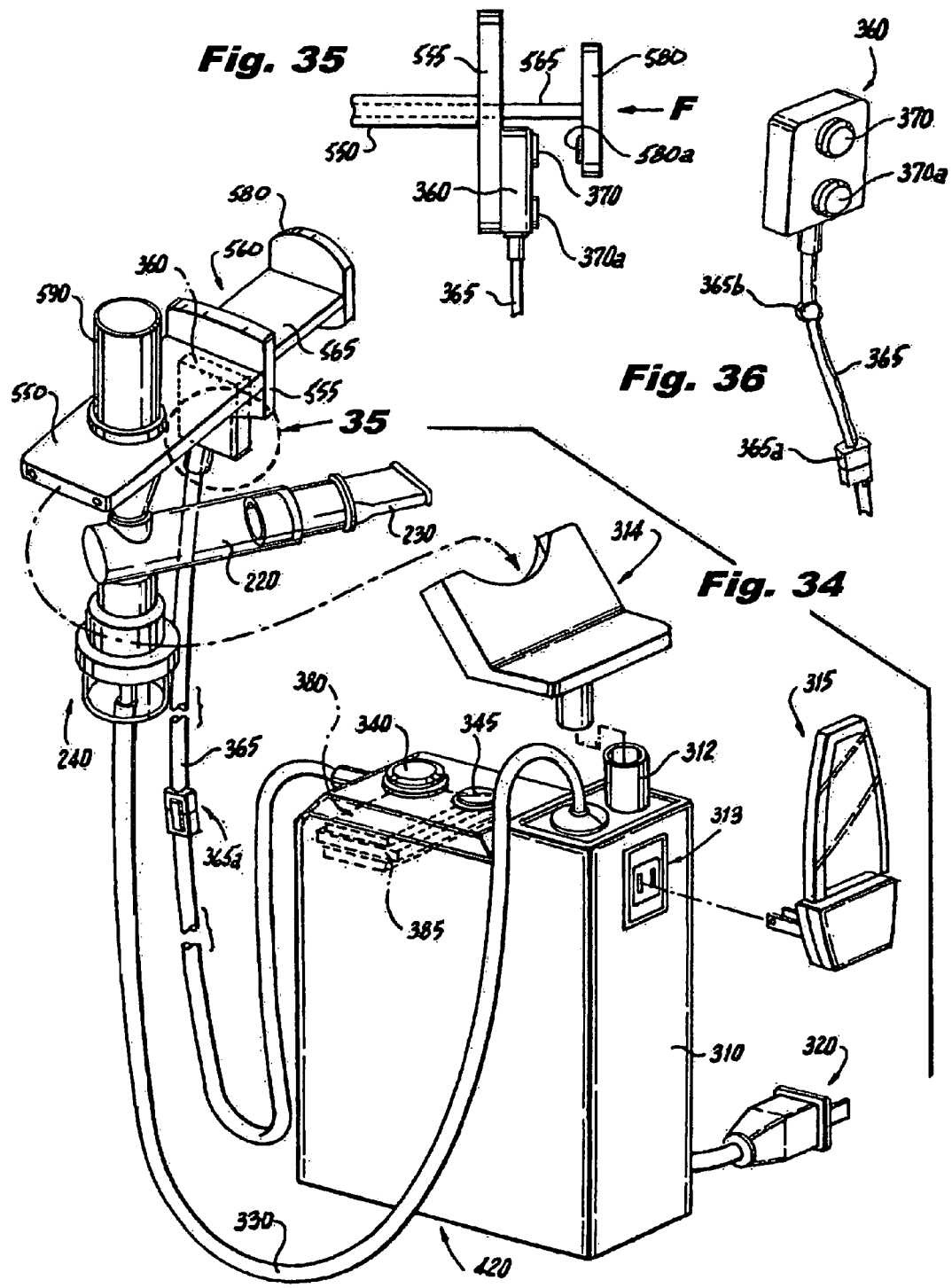

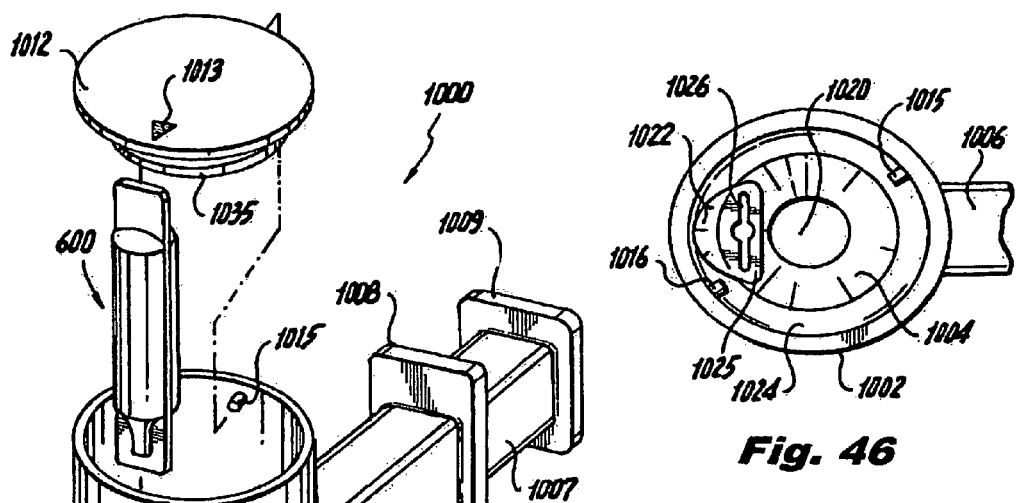
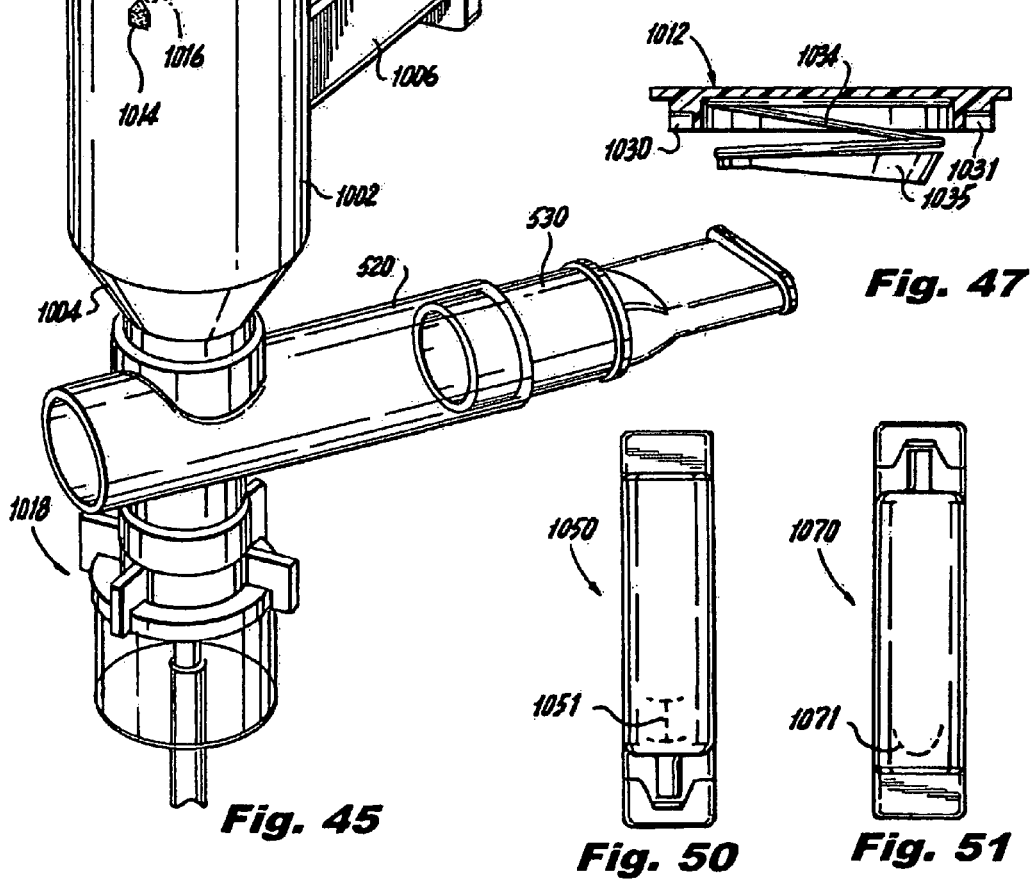
Fig. 45
Fig. 46
Fig. 47
Fig. 50
Fig. 51

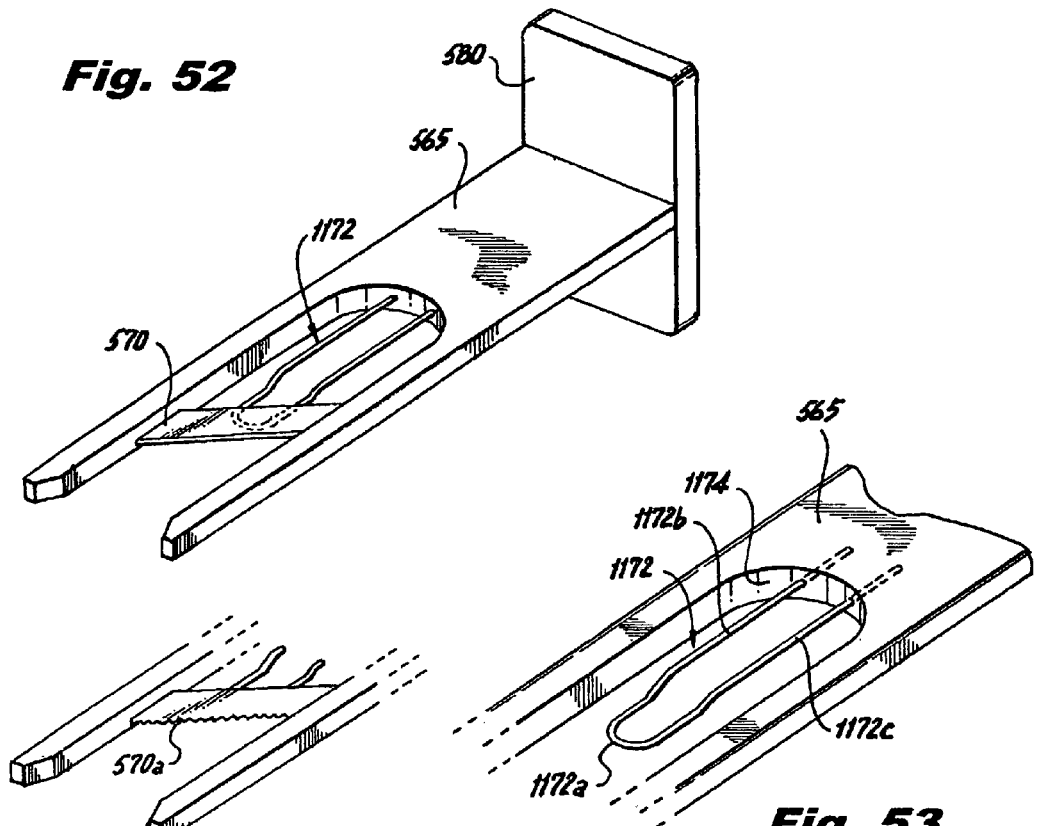
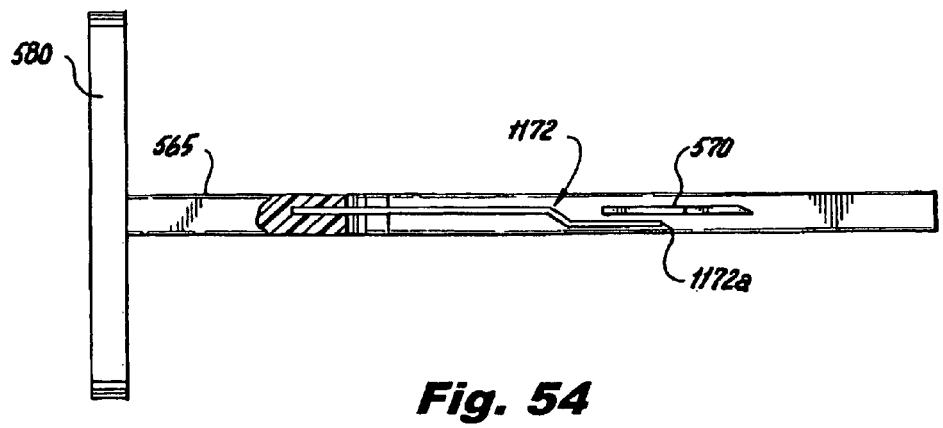

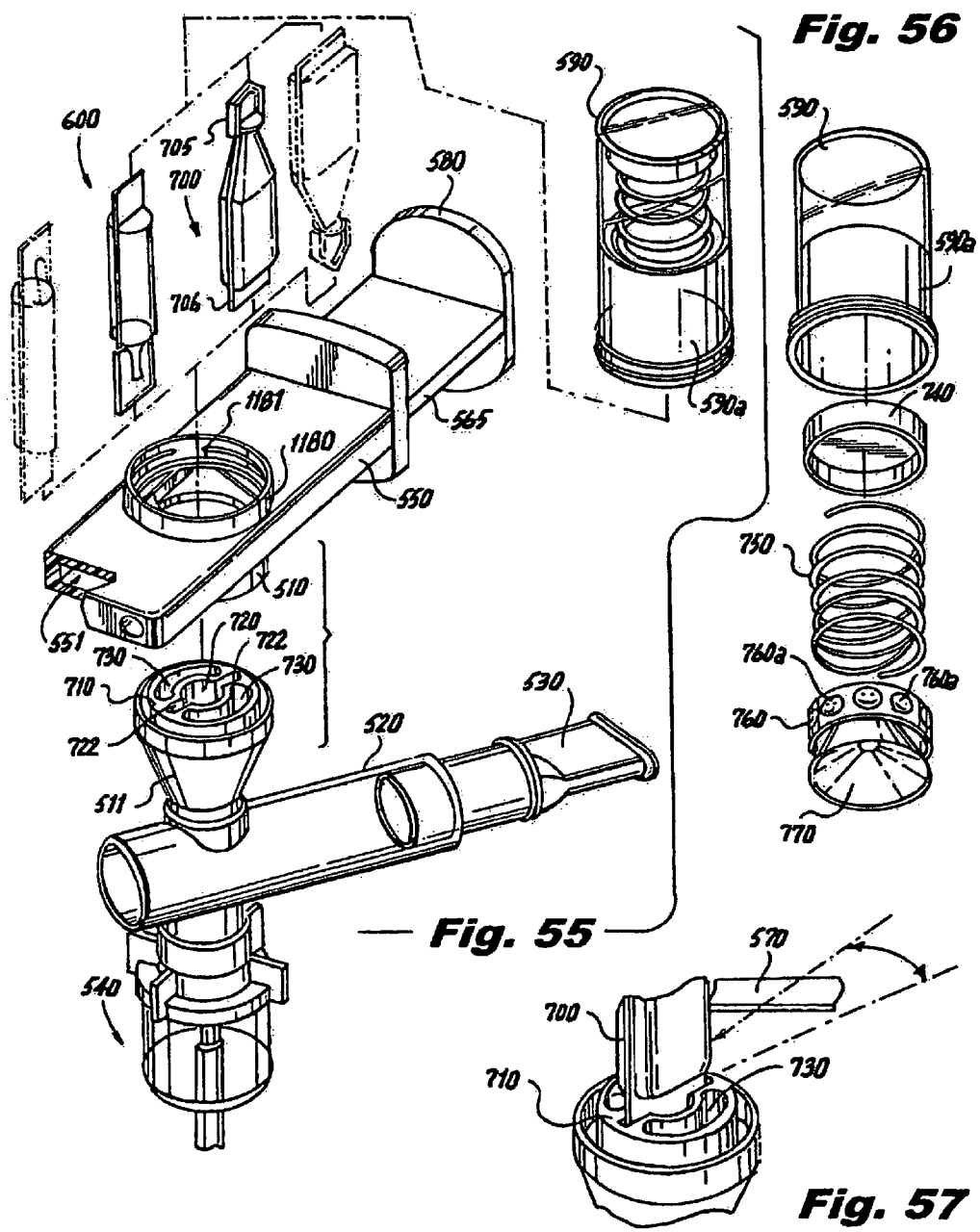

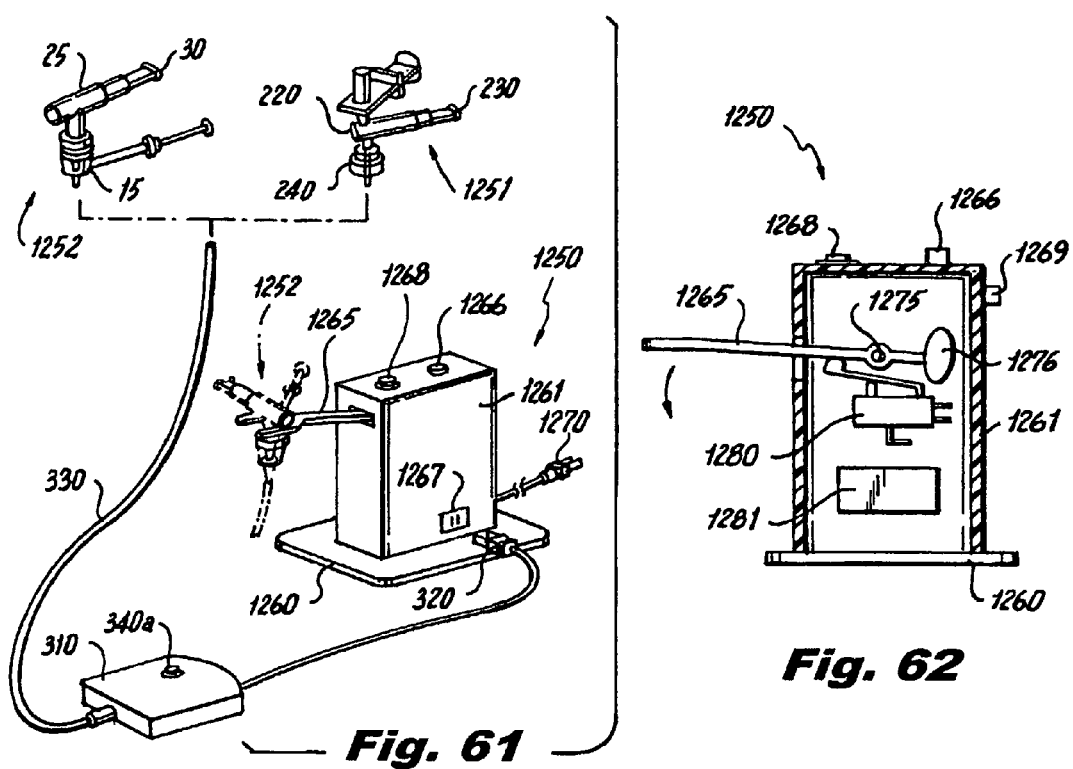
Fig. 61
Fig. 62
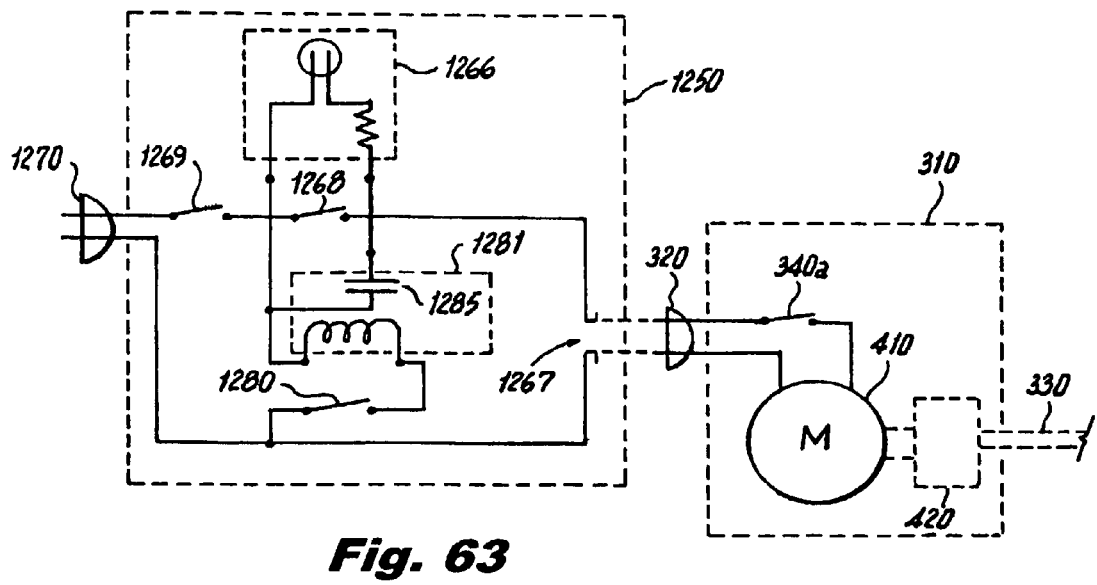
Fig. 63

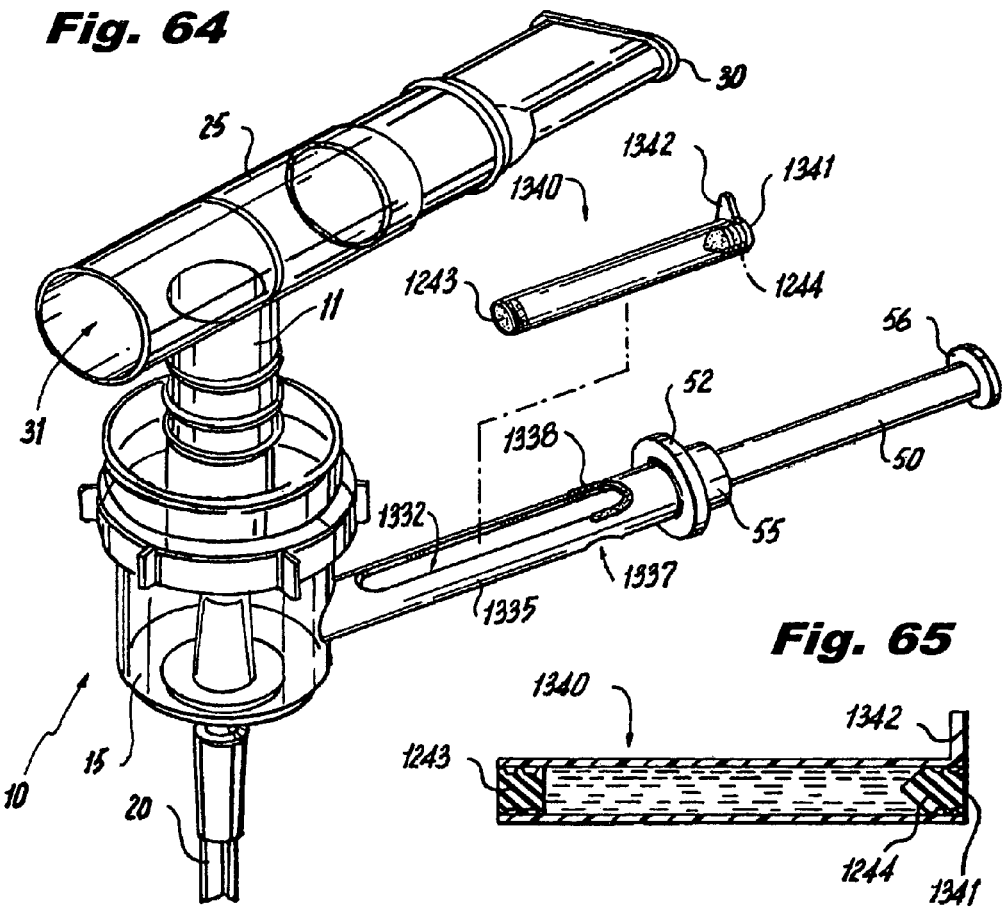
Fig. 64
Fig. 65
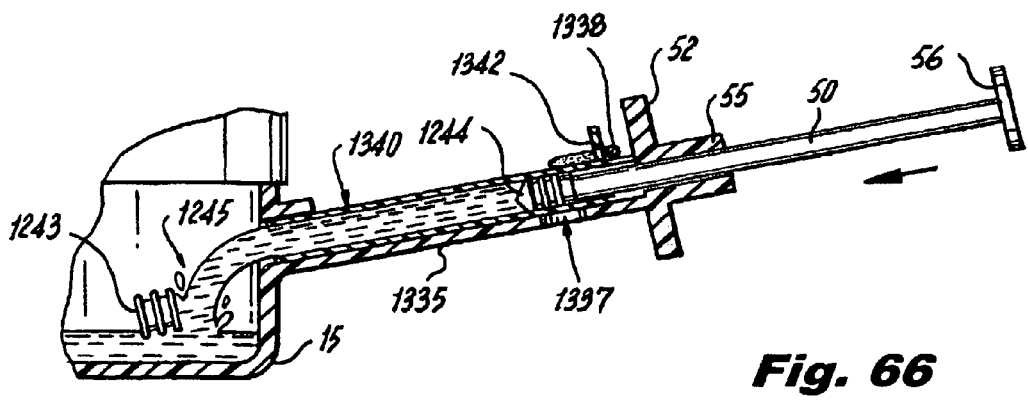
Fig. 66

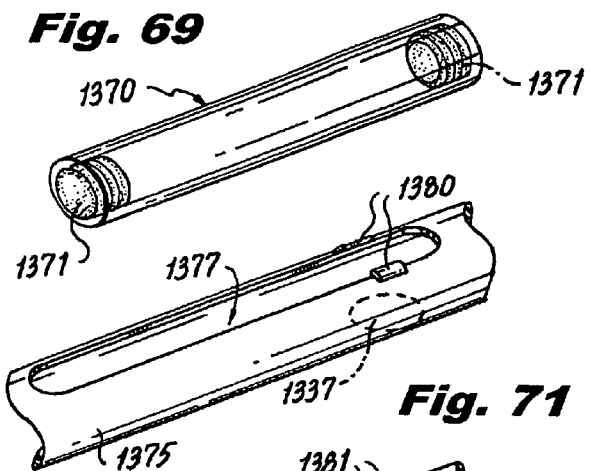
Fig. 69
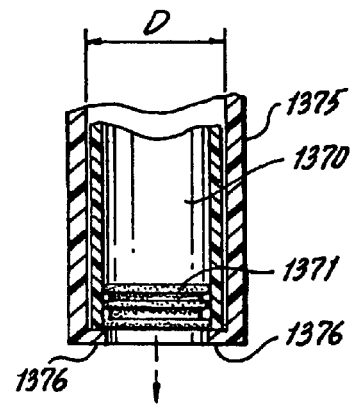
Fig. 70
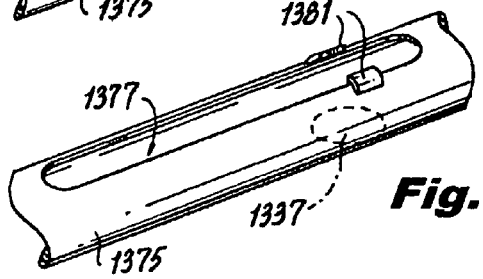
Fig. 71
Fig. 72
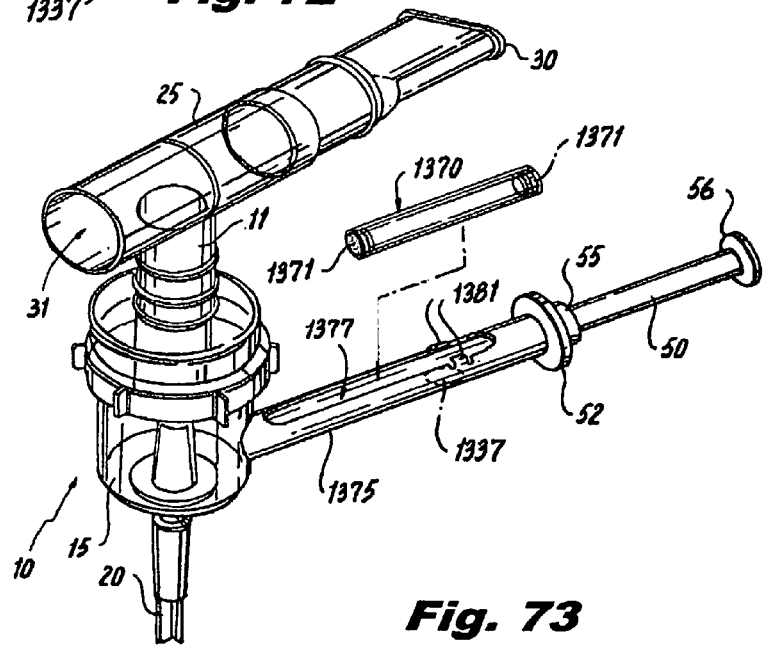
Fig. 73

CRADLE FOR SEMI-AUTOMATIC EMERGENCY MEDICATION DOSE NEBULIZER

RELATED APPLICATIONS

This application is a continuation of application Ser. No. 12/798,884 filed Apr. 13, 2010, which application is a continuation-in-part of application Ser. No. 12/380,135 filed Feb. 24, 2009, which application is a continuation-in-part of application Ser. No. 12/321,854 filed Jan. 26, 2009, now U.S. Pat. No. 7,814,902, which application is a continuation-in-part of application Ser. No. 12/283,303 filed Sep. 11, 2008, now U.S. Pat. No. 7,784,459, which application is a continuation-in-part of application Ser. No. 12/217,406, filed on Jul. 3, 2008, now U.S. Pat. No. 7,836,885, which application is a continuation in part of application Ser. No. 11/901,628, filed Sep. 18, 2007, now abandoned, which applications are incorporated by reference herein. This application claims priority in part under 35 U.S.C. §120 therefrom.

FIELD OF THE INVENTION

The present invention relates to a conventional nebulizer having a novel integral structure for conveniently delivering a dose of liquid medication to the conventional nebulizer's conventional nebulizing chamber

BACKGROUND OF THE INVENTION

Pulmonary medication may be needed by persons with breathing problems in a hurry. Typically a person experiencing an asthma attack is desperate to get medication. Often a single-shot hand-held rescue inhaler is medically inappropriate for treatment. In such cases, a misting nebulizer is needed. A misting nebulizer is an air pump device with a small plastic chamber attached to a mouthpiece. Prior art requires the nebulizer to be opened, liquid medication added to the chamber, the chamber closed and the pump started. The problem is that this series of steps requiring steady hands and manual dexterity may be difficult to achieve for an asthma attack sufferer who may be panicking because he/she can't breathe. Pulmonary medication may be needed by persons with breathing problems in a hurry. Typically a person experiencing an asthma attack is desperate to get medication. A nebulizer is an air pump device with a small plastic chamber attached to a mouthpiece. Prior art requires the nebulizer to be opened, liquid medication added to the chamber, the chamber closed and the pump started.

OBJECTS OF THE INVENTION

It is therefore an object of the present invention to provide a device for quickly and conveniently delivering a dose of liquid medication to the nebulizing chamber of a conventional nebulizer in an emergency.

It is a further object of the invention to provide reliable nebulized medication to a user in an emergency.

It is a further object of the invention to provide emergency nebulized medication to a user where the user is already in acute respiratory distress at the time the user locates the conventional nebulizer and has no person to assist with following the steps required to conventionally nebulize medication, to with: (1) to disassemble the nebulizer housing so as to expose the nebulizing chamber; (2) to locate a container capsule of liquid medication to be nebulized; (3) to open the liquid medication container, being careful not to spill it; (4) to squeeze the container capsule and to pour the liquid medication directly into the nebulizing chamber without losing any of it through spilling outside of the nebulizer chamber; (5) to reassemble the nebulizer housing; and (6) to position the inhaler mouthpiece in the mouth so as to inhale the nebulized medication.

It is a further object of the present invention to simplify the conventional procedure required to be followed by the user of a medication nebulizer, which conventional procedure may be critically complex for a person suffering from acute respiratory distress at the time the user locates the conventional nebulizer.

It is a further object of the preferred embodiment of the present invention to provide a simplified reliable process for deploying a dose of liquid medication in a nebulizer, comprising the steps of (1) deploy the medication with a single twist of a screw cap; and (2) inhale the nebulized medication.

It is a further object of the present invention to provide a novel medication dose delivery device built-in and integrated with a conventional nebulizer to accomplish the result of simplified reliable delivery of the liquid medication to the conventional nebulizing chamber by convenient user deployment without the need to disassemble and reassemble the nebulizer and to open and pour liquid medication at the time of an acute respiratory emergency.

It is a further object of the present invention to provide a conventional nebulizer having a stored single dose of liquid medication directly on board and integral with the conventional nebulizer in loaded-gun arrangement in preparation for use in an acute respiratory emergency.

It is a further object of the present invention to reduce the time needed for a person suffering an acute respiratory emergency to receive an effective dose of is nebulized medication, particularly where the suffering person has no readily available assistance in using a nebulizer.

It is a further object of the present invention to provide a nebulizer device with a stored dose of liquid medication where deployment of that dose is accomplished by a simple manual operation by a user.

It is a further object of the present invention to provide a method for speeding relief to sufferers of acute respiratory distress by reducing the time and effort required to deploy liquid medication in a nebulizer.

It is a further object of the present invention to provide reliable faster and simpler relief to a sufferer of acute respiratory distress who is alone and without assistance by reducing the time and effort required to deploy liquid medication in a nebulizer.

In keeping with the present invention other objects will make themselves clear to users of the device and to those of skill in the art, and thus this invention is not limited to the objectives here enumerated, which are not exhaustively presented and are described merely by way of example.

SUMMARY OF THE INVENTION

In keeping with these objects and others which may become apparent, the present invention relates to a conventional nebulizer having a novel integral structure for conveniently delivering a dose of liquid medication to the conventional nebulizer's conventional nebulizing chamber, the novelty being in providing a new structural component integral with the structure of a conventional nebulizer, whereby the liquid dose capsule is opened upon manual or automatic activation of an activator, such as a plunger with a capsule opener.

For example, the semi-automatic emergency medication dose nebulizer preferably includes a vertically extending housing having a nebulizer chamber containing medication in a dosage capsule. An opening in a bottom of the housing receives compressed air for nebulizing the medication contained within and released from the dosage capsule. A breather above the nebulizer housing is joined to the housing through a connecting tube extending vertically up from the housing for receiving the nebulized medication. The breather has a mouthpiece for use by a patient to receive the nebulized medication. An apparatus for refilling the nebulizing chamber with medication is mounted on and above the breather. A refilling tube or other configured chamber contains a storage chamber aligned with the connecting tube to receive the medication dosage capsule therein. Preferably, the storage chamber has a nesting base support for securing a lower end of the capsule in place. Preferably the storage chamber also includes an upper opening with a removable cap, which is configured to secure an upper end of the capsule in a preferred position, such as centrally located to encounter a severance blade, or, in another embodiment, along an anvil located at a side wall of the storage chamber when the cap is in place. The capsule may be held in place by a spring loaded conical or otherwise configured member mounted on an underside of the cap so that when the cap is positioned to close the top opening of the storage chamber, an edge of the member pushes the upper end of the medication capsule into the required position within the storage chamber.

The medication dosage capsule is opened by force, such as twisting or crushing. Preferably, however, a serrated severance blade severs the medication dosage capsule by slicing through a side of the capsule while the capsule is in the storage chamber, to release medication flowing by gravity into the nebulizing chamber. The severance blade preferably is a cutting blade mounted on a distal end of a holder, which is manually activated by a hand held plunger or is driven by an electric motor operable by a push button switch. The activation can be accomplished by an electronic push button causing operation of the plunger. The electric motor can be preferably a low output speed gear motor.

When a hand held plunger is used, the plunger includes a fixed finger or hand rest and a movable finger or hand rest attached to a distal end of the plunger, whereby squeezing the two rests together causes the plunger to advance toward the capsule. In another plunger embodiment, the plunger is driven by a pliers assembly for providing a mechanical advantage. The pliers assembly preferably includes a pair of pliers members having distal ends thereof attached to a fixed pivot bracket and a movable pivot bracket mounted on a distal end of the plunger, respectively, and pliers grips on proximate ends of the pliers members for exerting mechanical advantage in driving the plunger. The medication capsule can be severed by a horizontally oriented blade, or by a blade of another angular configuration, such as an obliquely slanted oriented blade or a vertically oriented blade, such as a replaceable cutting blade attached to a blunt crusher head, whereby the angularly oriented blade severs the capsule in a lower end and the optional crusher head crushes the capsule. Optionally the capsule can be crushed by a blunt crusher head itself without a blade, when the capsule has a built-in weakened area which bursts when pressure builds up within the capsule when the blunt crusher head comes in contact with the capsule.

It is further noted that, while the present invention is applicable to pulmonary conditions, such as asthma, it is contemplated that other medical conditions can be treated with misting medication where rapid deployment from a capsule is required. For example, nebulizers are described for use in treating diabetes with insulin in U.S. Pat. No. 5,451,569 of Wong et al, in treating human immuno-suppressed conditions in U.S. Pat. No. 7,388,076 and in cardiopulmonary resuscitation in U.S. Pat. No. 7,343,915 of Addington. Additionally U.S. Pat. No. 6,747,058 of Dedhiya et al describes dispensing medical marijuana through an aerosolizing nebulizer.

The preferable component is a chamber for vertically mounting the dosage capsule therein from above, wherein the capsule opener is a serrated blade cutting the capsule, or the capsule opener is a twist opener providing a torque application of twisting force to open the capsule to unload its contents directly into the misting chamber of the nebulizer. Besides the twisting force to open the capsule, the capsule may also be subject to crushing force, to overcome the ambient air pressure nominally holding the medication fluid in the capsule, and preventing it from flowing freely through the narrow aperture at the discharge end of the medication capsule.

Alternatively, the plunger can also automatically start the electrical components of the compression chamber for nebulizing a mist.

The novel structural component comprises a storage chamber for storing, in loaded-gun fashion, a dose of liquid medication on board the conventional nebulizer housing with a simple user-operable blade plunger capsule opener opening the medication capsule needed to deploy the medication into the conventional nebulizing chamber. The novel structure medication storage chamber generally has an open-aperture delivery end disposed in close proximity to the nebulizing chamber so that the liquid medication, when deployed by a user, flows reliably and directly into the nebulizing chamber.

The novel medication storage chamber of the non-preferred embodiment accepts a single disposable and user-replaceable cartridge capsule containing a dose of medication to be nebulized in an emergency. The chamber is provided at its outer end with plunger having a capsule opener for a user to open the medication capsule. The blade may be generally horizontal in orientation, so that the capsule is severed, wherein the severed bottom portion of the capsule below the blade severance contact area falls out of the way to permit fluid flow by gravity therefrom into the nebulizer misting chamber. Optionally the blade can be vertically or angularly oriented at an oblique angle.

For example, the semi-automatic emergency medication dose nebulizer preferably includes a vertically extending housing having a nebulizer chamber containing medication in a dosage capsule. An opening in a bottom of the housing receives compressed air for nebulizing the medication contained within the capsule. A breather above the nebulizer housing is joined to the housing through a connecting tube extending vertically up from the housing for receiving the nebulized medication. The breather has a mouthpiece for use by a patient to receive the nebulized medication. An apparatus for refilling the nebulizing chamber with medication is mounted on and above the breather. A refilling tube contains a storage chamber aligned with the connecting tube to receive the medication dosage capsule therein. A severance blade severs the medication dosage capsule by slicing through a side of the capsule while the capsule is in the storage chamber to release medication flowing by gravity into the nebulizing chamber.

The severance blade preferably is a serrated blade mounted on a distal end of a holder, which is manually activated by a hand held plunger or is driven by an electric motor operable by a push button switch.

The electric motor can be preferably a low output speed gear motor. In the push button embodiment, a switch initiates operation of the electric motor to advance the holder from an initial position until the cutting blade severs the medication dosage capsule, allowing the medication to flow into the nebulizing chamber.

In the preferred embodiment, the severed capsule is held by a capsule holder with one or more fluid apertures. In the blade cutting embodiment, optionally a rigid or slightly flexible capsule follower accompanies the cutting blade to push the remnants of the severed U-shaped capsule out of the way after severance of the capsule. Preferably, the capsule follower is a forwardly extending loop made of a looped high grade metal, such as a non-corrosive stainless steel rod or a synthetic material, such as plastic. Optionally the loop can be made of a coated metal coated by a non-metallic coating. It is positioned so that its arcuate end is under the rear edge of the cutting blade, so that there is a smoother transfer of the severed capsule to the follower. The follower is preferably a looped rod, to maximize the open fluid flow region, while supporting the severed capsule. The fluid flow region has a curved rear edge which conforms to a curved rear portion of the medication capsule retaining region. Also the follower is used to separate the cut capsule to insure that all liquid is able to drain into nebulizer. The follower is small enough to insure fluid flow during the pushing of the severed capsule portions out of the way.

When the capsule is severed by the serrated blade at an appropriate wide portion that ambient air pressure is not a factor, the capsule may not need to be crushed. Fluid flows freely through the severed capsule without being crushed. The simplest emergency user-pressure means is a plunger one-hand aperture arrangement which permits a quick opening of the medication capsule to dispense the fluid therefrom.

The novel combination of medication dose capsule with a conventional nebulizer provided in the present invention addresses and solves the problem of what procedure must be followed by a patient having a breathing emergency, such as a severe attack of asthma, and needs a quick reliable dose of nebulized medication, particularly where (1) no other person is available to assist the patient and (2) a single-shot hand-held nebulizer rescue inhaler is medically inappropriate for treatment.

In a further embodiment, the blade plunger is advanced toward the medication capsule and the cutting action is accomplished by power provided by a small motor. A push-button is pressed by the user initiating an automatic sequence starting the motor, advancing the blade plunger toward the capsule, then instantly reversing the motor after the cut is accomplished to withdraw the plunger back toward the starting position and shutting down. This makes the cutting far more feasible for a large community of asthma sufferers who may have other ailments restricting the force they can exert with their fingers.

The apparatus for this embodiment includes preferably a DC permanent magnet (DCPM) motor supplied with low voltage DC of 6-12 volts through a simple control circuit. One implementation described uses a motor coupled via two meshed gears driving a lead screw. The gear set reduces the motor speed while increasing torque to drive the lead screw. The lead screw nut is attached to a movable blade plunger guided within a linear guide. A second alternate implementation described uses a low speed output DCPM gearmotor with a small gear pinion attached. The pinion engages a linear gear rack that is integral to a movable blade plunger guided by a linear guide. In either case, limit switch elements at both motion extremes are used to interface with the control circuit. These limit switches can be as simple as snap action switches or magnetic reed contacts, or they can be implemented as optical or Hall Effect sensors. The choice is properly made as the control circuit is defined. This can be as simple as the relay logic described, or more complex solid state or processor driven circuits can be implemented.

Other embodiments are concerned with yet other manual methods for quickly extracting nebulizer medication from capsules. A larger vertical storage chamber is used in these embodiments. A concave anvil support region within the chamber helps support the medication capsule along its side during medication extraction. A spring-loaded conical member attached to the storage chamber cap guides the medication capsule into the anvil cavity to insure proper positioning.

In one embodiment, a directly actuated plunger with attached vertically oriented blade (at the distal end) is used to pierce the medication capsule near its bottom end within the vertical storage chamber.

In another embodiment, modified medication capsules with an intentionally weakened region at the lowest end (as inserted into the chamber) are used exclusively. Instead of a blade, a blunt crusher head is at the distal end of the plunger. When forced against the medication capsule, internal gas pressure build-up causes the weakened region to rupture, immediately spewing the medication out within the storage chamber. Also, this embodiment uses pliers grips as a mechanical advantage device to multiply the force exerted on the end of the plunger. (Note that this method can also be used on the embodiment with the vertical or obliquely oriented blade described above.)

In a further embodiment, as in an earlier embodiment of this invention, a medication storage chamber extends outward through the wall of the nebulizing chamber. The medication dose cartridge for use with a piston rod impinging on an internal elastomeric piston seal now has a uniform diameter from end to end. It's inner end (at the nebulizing chamber) is now sealed with an elastomeric seal not unlike the piston at the other end; the medication is stored between these two elastomeric seals. It is understood that any force on the piston rod will be converted to hydraulic pressure of the medication dose which produces a like force on the elastomeric seal at the inner end. As pressure builds up, the seal friction against the inner diameter of the medication dose cartridge will be overcome; the seal will be ejected into the nebulizing chamber thereby releasing the medication dose into the chamber.

An accessory for the nebulizers of this invention is a nebulizer cradle tower. The function of this tower is to support the nebulizer with medication dose poised for release and insure that lifting the nebulizer off its cradle will automatically start the compressor in preparation for use. This is to minimize the set-up and insure start-up without fumbling while the user is in distress during an asthma attack. This is compatible with either of the side-storage capsule embodiments using a piston rod plunger as well as the vertical storage chamber embodiment using a capsule cutter. The nebulizer cradle tower presets all the electrical components with switches in the proper positions and indicates a "standby" readiness which should immediately start the compressor once the nebulizer is lifted off the cradle on which it rests. Thus all the preset conditions can be handled during a non-panic phase. The electrical components of the tower include a line cord with wall plug, a 110 VAC relay, a cradle switch, an emergency bypass switch, a system on/off switch, and a 110 VAC outlet. A 110 VAC indicator lamp with green lens signals proper set-up when the nebulizer is supported by the cradle. The green lamp glowing indicates that the tower is plugged into a powered wall outlet, the system on/off switch is on, the emergency switch is OFF, the compressor is plugged into the tower, and the compressor motor switch on the compressor housing in the ON position.

Other embodiments show variations in design of medication cartridge and associated medication storage chamber. Another embodiment relates to the position and attachment of the medication dose storage chamber.

BRIEF DESCRIPTION OF THE DRAWINGS

The present invention can best be understood in connection with the accompanying drawings. It is noted that the invention is not limited to the precise embodiments shown in drawings, in which:

FIG. 3 shows a perspective view of one embodiment having a conventional nebulizer having a novel built-in medication storage chamber extending outward from the housing of the nebulizer;

FIG. 4 shows a medication dose cartridge having an inner end with tapered shoulders so as to be capable of nesting within the medication storage chamber shown in FIG. 3; the medication cartridge has an outer end having means of accepting force for the purpose of ejecting the liquid medication contained in the cartridge through its inner end and into the nebulizing chamber;

FIG. 5 shows a detail of the embodiment of FIGS. 3 and 4, with the medication storage chamber extending outward from the nebulizing chamber through the wall of the nebulizer housing, having a medication dose cartridge therewithin and having a piston for application of force by a user to break the seal of the medication cartridge. The injection nozzle of the medication storage chamber is shown in close proximity to the nebulizing chamber within the housing;

FIG. 6 shows an exploded view of a second embodiment, having a vertical storage sleeve for a capsule of liquid medication, where the capsule is seated with its tear-off tab in close proximity to the conventional nebulizing chamber within the housing of the conventional nebulizer;

FIG. 7 shows a detailed crossectional view in cutaway of the twist open embodiment of FIG. 6;

FIG. 8 shows an exploded view of a third embodiment of the preferred embodiment, having a vertical storage sleeve for a capsule of liquid medication, where the capsule is seated with its tear-off tab in close proximity to the conventional nebulizing chamber within the housing of the conventional nebulizer;

FIG. 9 shows a top exploded view of the third embodiment of FIG. 8, having a vertical storage sleeve for a capsule of liquid medication, showing a lever twisting the capsule, while the tear-off portion of the capsule is seated and immobilized, so that twisting of the capsule causes a tear and crushing of the capsule between the tear-off portion and the fluid reservoir portion;

FIG. 10 is a close-up detail crossectional view in cutaway of the third embodiment in FIGS. 8 and 9, showing the rotation of the capsule while the tear-off portion is seated immobile in place;

FIG. 11 is a close-up detail bottom view of the sleeve of FIGS. 8, 9 and 10 showing the restraining stop means and mist-accommodating ports;

FIG. 12 is an exploded perspective view of an alternate fourth embodiment for a knob cam activation assembly for dispensing medication from a capsule;

FIG. 13 is a bottom view of the knob cam activation assembly shown in FIG. 12;

FIG. 14 is a top plan view of the knob activator thereof;

FIG. 15 is a bottom view of the knob activator as in FIG. 14;

FIG. 16 is a bottom view of the cam assembly shown in FIG. 12.

FIG. 17 is a perspective view of an alternate fifth embodiment for the nebulizer of this invention showing a flat blade plunger guide with a blade plunger in the extended position for slicing and cutting open the medication capsule;

FIG. 18 is a top view of the blade plunger assembly as in FIG. 17;

FIG. 19 is a crossectional side view detail thereof, showing the medication dosage capsule in the vertical storage chamber prior to the cutting operation;

FIG. 20 is a top plan crossectional detail view of the cutting blade approaching the medication dosage capsule to be severed;

FIG. 21 is a side crossectional view detail thereof, showing the cutting blade in contact with the medication dose capsule at the initiation of the cutting operation;

FIG. 22 is a side crossectional view detail of the medication dosage capsule in the vertical storage chamber just after having been cut with medication flowing through the plunger flow aperture into the lower section;

FIG. 23 is a perspective view of the entire nebulizer system of the fifth embodiment of this invention including the nebulizer assembly along with the compressor housing.

FIG. 24 is a perspective view of a sixth embodiment for a blade plunger assembly;

FIG. 24A is a close up side crossectional view showing a tongue and groove orientation sub-assembly, as viewed in dashed circle line "24A" of FIG. 24;

FIG. 24B is a close-up side crossectional detail view of another embodiment for an orientation sub-assembly for the blade plunger assembly;

FIG. 24C is a close-up front elevational view of the plunger portion thereof;

FIG. 24D is a top plan view of the plunger guide of the orientation subassembly of FIG. 24B;

FIG. 25 is a close-up perspective detail view of a follower paddle behind the cutting blade in the plunger assembly of FIG. 24;

FIG. 29 is a perspective exploded view of a seventh embodiment of nebulizer with enhanced medication capsule holding features;

FIG. 30 is an exploded perspective view of coil spring hold-down elements within a storage chamber cap;

FIG. 31 is a perspective detail view of the medicine capsule base holder, showing a cutting blade approaching a medication capsule, wherein the angle and arrow lines depict a blade cutting angle orientation;

FIG. 32 is a side crossectional medicine capsule chamber prior to cutting;

FIG. 33 is a partial side crossectional of the medicine capsule chamber just after cutting showing medicine flow downward;

FIGS. 34-37 show a fully activated nebulizer system where activation of the capsule opening plunger also activates the nebulizer pump circuit;

FIG. 45 is a perspective view of a nebulizer vertical storage chamber assembly with direct acting manual plunger;

FIG. 46 is a top view of the interior of the vertical storage chamber showing the anvil cavity and lower medication capsule support extension;

FIG. 47 is a side elevation in partial crossection of the vertical storage chamber cap with spring-loaded conical member;

FIG. 50 is a front view of a medication capsule with a weakened region at the normal bottom end;

FIG. 51 is a front view of a medication capsule as in FIG. 50 but with the weakened region of different configuration at the opposite end;

FIG. 52 is a perspective view of another embodiment for a blade plunger assembly;

FIG. 52A is a close-up detail view of a preferred embodiment for a serrated severance cutting blade;

FIG. 53 is a close-up perspective detail view of a looped follower paddle located behind the cutting blade in the plunger assembly of FIG. 52;

FIG. 54 is a side elevational view thereof;

FIG. 55 is a perspective exploded view of the nebulizer using the blade plunger assembly of FIG. 52;

FIG. 56 is an exploded perspective view of coil spring hold-down elements within a storage cap; FIG. 57 is a perspective detail view of the medication capsule base holder, showing a cutting blade approaching a medication capsule, wherein the angle and arrow lines depict a blade within orientation.

FIG. 61 is a perspective view of a nebulizer cradle tower accessory.

FIG. 62 is a side view in partial crossection showing the major components within a nebulizer cradle tower;

FIG. 63 is a wiring diagram of a nebulizer cradle tower;

FIG. 64 is a perspective view of a nebulizer with side storage chamber using a medication dose cartridge with a uniform diameter and a tail extension;

FIG. 65 is a side crossectional view of a medication cartridge with a tail extension;

FIG. 66 is a side crossectional view of a medication cartridge with tail extension emptying into a nebulizing chamber;

FIG. 69 is a perspective view of a medication cartridge of simplified design;

FIG. 70 is an enlarged crossectional detail of the fit of the medication cartridge of FIG. 69 within the end of a storage chamber;

FIG. 71 is a detail of the loading slot of a storage chamber using elastomeric bumps;

FIG. 72 is a detail of the loading slot of a storage chamber using molded spring extensions; and, FIG. 73 is a perspective view of a nebulizer with a sideways loading storage chamber using a medication cartridge of simplified design.

LIST OF REFERENCE NUMERALS

Figure 1:
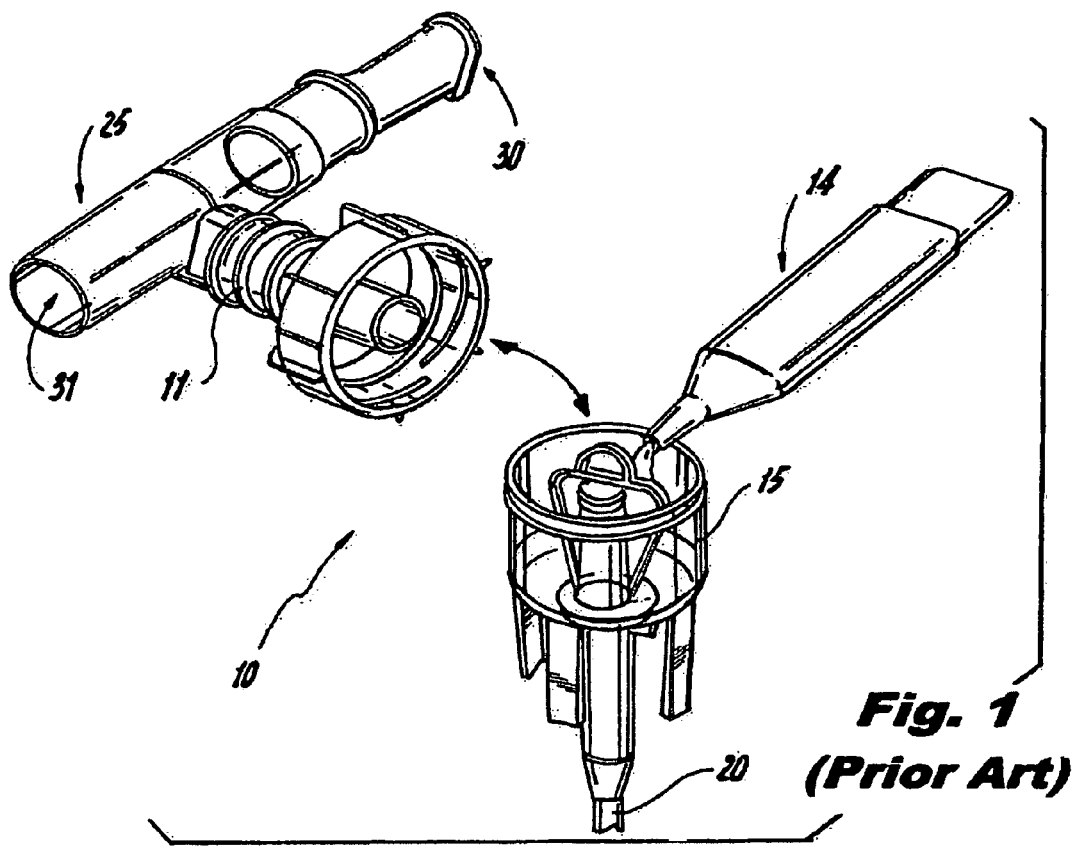
FIG. 1 shows an exploded view of a prior art nebulizer disassembled to illustrate pouring of medication into the nebulizing chamber.
Figure 2:
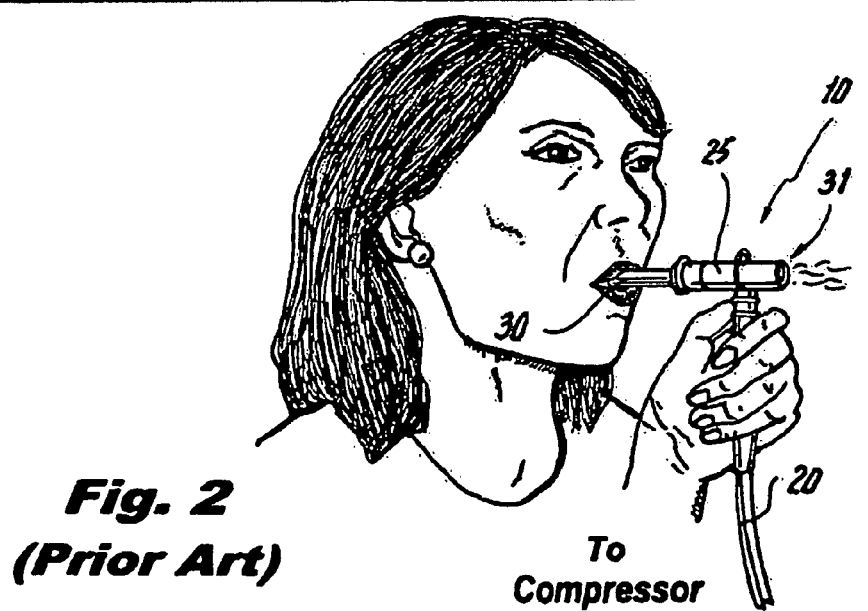
FIG. 2 shows a user operating a conventional prior art nebulizer by breathing through the mouthpiece.

10 Nebulizer Housing
11 Connecting Tube between nebulizer housing 10 and breather 25
14 Conventional medication dose container including nebulizer chamber
15 Nebulizer chamber
20 Compressed air supply line
25 Conventional breather portion of conventional nebulizer
30 Conventional mouthpiece at proximal end of conventional breather 25
31 Open distal end of conventional breather 25
32 Inside surface of novel storage chamber
35 Novel storage chamber for medication dose
36 Inner end of medication storage chamber 35
37 Outer end of medication storage chamber 35
38 Tapered open-ended nozzle at inner end 36 of medication storage chamber 35
40 User-removable user-replaceable medication dose cartridge containing a dose of liquid medication to be nebulized
41 Outer end of medication dose cartridge 40
42 Inner end of medication dose cartridge 40
43. Pressure seal at inner end 42 of Medication dose cartridge 40.
44. Elastomerically Sealed Piston at outer end 41 of cartridge 40.
45. Open reduced-diameter inner end of Medication dose cartridge 40.
47. Tapered inner shoulders of medication Cartridge 40.

50. Grooved piston rod.
52. Finger engagement wings.
55. Stop for engaging groove of Piston Rod 50
56. Pressure plate at the end of Piston Rod 50 for application of user force.
62. Vertical medication storage sleeve 62.
62a, 62b. Slots in sleeve 62 to allow fluid to enter reservoir 15
62c. Restraining stop means for tear off portion of capsule 66
62d. aperture for fluid flow into reservoir 15
64. Tear off tab.
66. Medication dose capsule.
68. Screw cap activating handle.
69. Activating lever handle.
69a. Activating lever handle rod.
69b. Activating lever handle paddle.
70. Inhaling pipe.
162a. Mist port.
162b. Mist port.
162c. Restraining stop means.
168. Knob activator.
180a. Capsule pincher blade.
180b. Capsule pincher blade.
190. Cam assembly.
192a. Cam contact element.
192b. Cam contact element.
194a. Rotation stop element.
194b. Reciprocating rotation stop element.
200 Nebulizer assembly with blade cutter.
210 Vertical storage chamber.
220 Inhalation tube.
230 Mouthpiece.
240 Conventional nebulizing chamber.
250 Flat blade plunger guide.
255 Fixed finger/hand grip.
260 Blade plunger assembly.
265 Flat blade plunger.
270 Cutting blade.
275 Plunger flow aperture.
280 Plunger finger/hand grip.
290 Storage chamber cap.
292 Drainage weep hole in plunger guide.
295 Cap covering drainage weep holes.
300 Medication dosage capsule.
300a Severable distal end portion of medication capsule 300.
310 Conventional compressor housing.
311 Integrated compressor housing.
312 Locator light indicator and holder support.
313 Night light plug receptacle.
314 Nebulizer holder.
315 Night light.
320 Electrical wall plug.
330 Compressed air line.
340 Manual compressor switch.
340a Manual rocker switch of conventional compressor
345 Indicator lamp.
360 Plunger switch.
365 Plunger switch cable.
365a Switch cable connector
365b LED denoting standby mode
370 "ON" button of plunger switch
370a "OFF" button of plunger switch
380 Relay.
385 Transformer.
390 Relay coil.
395 Relay contacts.
410 Compressor motor.
420 Air compressor.
500 Nebulizer assembly with blade cutter and pusher.
510 Vertical storage chamber.
510a Capsule retaining guide opening
510b Capsule retaining guide
511 Base of capsule holder 710
520 Inhalation tube.
530 Mouthpiece.
540 Conventional nebulizing chamber.
550 Flat blade plunger guide.
551 Hollow pocket in plunger guide 550.
552 Inner wall tongue.
552a Inner wall protrusion button.
552b External misorientation stop.
553 Inner wall groove.
553a Inner wall top groove.
554 Capsule stabilizer block.
554a Sloping capsule guide.
555 Fixed finger grip.
556 Capsule guide
560 Blade plunger assembly.
565 Flat blade plunger.
565a Optional flat blade plunger
565b Finger/hand grip of flat blade plunger 565a
570 Cutting blade
570a Serrated edge of cutting blade
572 Follower paddle of cutting blade 570.
572a Optional follower paddle of cutting blade 570
572b Slanted sides of optional follower paddle 572a
572c Slot for blade 570
572d Slanted orientation edge
572e Beveled inside edge of optional flat blade plunger 565a
573 Aperture in blade plunger 570
574 Optional plunger guide
574a Slanted side of plunger guide
575 Hollow discharge tube.
576 Screen.
580 Plunger finger/hand grip.
580a Bumper button contact on plunger finger/hand grip 580.
590 Storage chamber cap.
590a Opaque bottom of cap 590.
600 Medication dosage capsule.
600a Severed distal end portion of medication capsule 600.
700 Alternate style medication dosage capsule.
705 Pointed top end of dosage capsule 700.
710 Medication capsule base holder.
720 Central hole with slots in base holder.
722 Slots of control hole 720.
730 Peripheral holes in base holder to permit medication flow.
740 Top fixed spring retainer.
750 Coil spring.
760 Bottom movable spring retainer.
760a Indicia on retainer 760.
770 Conical top holder for medication capsule.
800 Auxiliary power box.
802 Nebulizer plug outlet.
803 Night light outlet.
815 Night light.
850 Lead screw type powered blade plunger.
851 Push button for powered plunger versions.
852 DCPM motor.
853 Housing of lead screw powered blade plunger.

856 Motor gear for lead screw version.
857 Large lead screw drive gear.
858 Lead screw.
859 Lead screw nut.
860 Grooved linear guide for lead screw version.
861 Plunger carriage attached to 859.
863 Blade holder assembly-front part of 861.
865 Limit switch for reversing.
866 Limit switch for shut down.
900 Rack and pinion (r&p) version of powered blade plunger.
901 Housing of r&p version.
902 DCPM gearmotor.
903 Grooved linear guide for r&p version.
910 R&p plunger carriage.
911 Blade holder assembly-front part of 910.
912 Rack teeth.
914 Edge operating reversal limit switch.
915 Motor pinion gear engaged with 912.
950 AC/DC power supply for motor driven blade plunger.
952 Capacitor.
954 Single-shot timing pulse.
956 Relay driver.
958 Isolation diode.
960 Isolation diode.
962 Power relay.
964 Reverse control relay.
966 Motor reversing relay.
1000 Vertical storage chamber assembly with direct actuation
1002 Large vertical storage chamber
1004 Funnel region to collect and guide medication
1006 Plunger housing
1007 Plunger rod
1008 Fixed finger/hand rest
1009 Movable finger/hand rest
1012 Storage chamber cap
1013 Indicia for cap lock line-up
1014 Indicia on chamber for cap line-up
1015 Large diameter lock pin
1016 Small diameter lock pin
1018 Hollow extension
1020 Central hole above nebulizer chamber
1022 Anvil support recess
1024 Chamber base support ring
1025 Medication capsule support extension
1026 Capsule end slot
1030 Small pin slot
1031 Large pin slot
1034 Leaf spring
1035 Conical member
1041 Vertical piercing blade
1045 Vertical storage chamber assembly with pliers grips
1046 Plunger housing
1047 Plunger
1050 Modified capsule
1051 Weakened region of modified capsule
1053 Blunt crusher head
1055 Fixed pivot bracket
1057 Movable pivot bracket
1059 Central pivot
1060 Pliers grip
1061 Pliers grip
1070 Modified capsule
1071 Weakened region of modified capsule
1172 U-shaped looped rod
1172a Distal curved end of looped rod
1172b Prong of looped rod
1172c Prong of looped rod
1174 Curved wall of fluid flow region of blade plunger 565
1180 Upwardly extending edge wall of capsule plunger guide 5
1181 Inside surface of edge wall 1180
1232 Inside surface of novel storage chamber
1235 Novel storage chamber for medication dose
1237 Outer end of 1235
1240 Medication dose cartridge with uniform diameter
1241 Outer end of 1240
1242 Handle and locator flange
1243 Elastomeric inner end seal
1244 Elastomeric piston seal
1245 Open inner end of cartridge 1240 spilling into nebulizing chamber
1250 Nebulizer cradle tower
1251 Nebulizer assembly with vertical storage chamber and cutter
1252 Nebulizer assembly with side storage chamber and piston rod
1260 Base of tower
1261 Housing of tower
1265 Nebulizer holding cradle
1266 Indicator lamp
1267 Electrical outlet for compressor
1268 Emergency bypass switch
1269 System on/off switch
1270 Wall plug for nebulizer cradle tower
1275 Cradle pivot
1276 Cradle counterweight
1280 Cradle switch
1281 Relay
1285 Relay contact pair
1332 Loading slot for cartridge
1335 Storage chamber
1337 Cartridge push-out hole
1338 Elastomeric edge around end of loading slot
1340 Medication dose cartridge with tail extension
1341 Outer end of 1340
1342 Tail extension
1350 Modified storage chamber for vertical usage
1351 Stainless steel tube
1352 Cross tube with bulge
1353 Enlarged down tube
1370 Simplified medication cartridge
1371 Elastomeric seals
1375 Storage chamber for simplified cartridge
1376 Storage chamber end ridge
1377 Load slot for simplified cartridge
1380 Elastomeric retaining bumps
1381 Molded retaining extensions

DETAILED DESCRIPTION OF THE INVENTION

In keeping with the objects of the invention, the present invention provides a conventional nebulizer having a built-in (and thus integral) novel storage structure for storing a dose of liquid medication in preparation for an emergency. The liquid medication is conveniently delivered to the conventional nebulizer's conventional nebulizing chamber.

A conventional nebulizer is used to aerosolize liquid medication and deliver the aerosol for inhalation by a user. Although both are typically used for treating pulmonary medical conditions such as asthma, a conventional nebulizer differs from hand-held inhaler sprayers in that the hand-held aerosolizer generally contains multiple doses of medication, has a propellant permanently loaded within it, and is indicated for use where a single aerosolized dispensed quantity comprises the intended dose of medication for use by a patient.

It is critical to accurately time the dispensing shot from a hand-held medication inhaler to coincide with a user's inspiration, so as to ensure that the medication actually reaches the lungs of a user. Mistiming of the dispensing shot from a handheld inhaler can result in a short dose of medication or in no dose at all.

A conventional nebulizer, in contrast, has no stored medication at all. It is comprised of a nebulizing chamber, an air pump and an inhaler. The air pump, usually electrically driven, supplies a stream of compressed air through a conduit to a nebulizer housing. The housing is generally cylindrical, has a top and bottom part that can be separated by a user, and the top part has an upwardly projecting extension that ends in an inhaler. The inhaler is generally a horizontally disposed tube with an open distal end and a proximal end that is an open-ended mouthpiece.

The conventional nebulizer housing contains a nebulizing chamber. The chamber is basically a vertical cylinder with an open top for receiving a dose of liquid medication. The chamber has an air-stream inlet in the bottom. Compressed air from the air pump is conveyed to the chamber's bottom air inlet through a conduit. The compressed air enters the bottom of the nebulizing chamber and is then mixed with the dose of liquid medication, causing the medication to become nebulized into an aerosol. There is an open airflow between the nebulizer chamber and an upwardly extending short tube leading to a T-connection with a horizontal tube open at both ends that comprises an inhaler pipe with a breather mouthpiece is at one end. One open end of the inhaler pipe comprises a distal end, opposite to a proximal end which comprises the mouthpiece shaped to fit into the mouth of a user.

The inhaler pipe is in open airflow with the nebulizer chamber. When a user inhales through the proximal open end of the mouthpiece, air is urged into the open distal end and into the proximal end of the mouthpiece. The user's inhalation effort also urges air from the nebulizer chamber, containing nebulized medication to rise up the connecting tube and to enter the proximal end of the mouthpiece.

The user thus inhales nebulized liquid medication, and the user may do so with inhalations repeated as needed over a period of time sufficient to get relief from respiratory symptoms that put the user into acute distress, such as an asthma attack.

Thus an important difference between a conventional nebulizer and a hand-held inhaler is that the hand-held device is intended to deliver a single dose of medication intended to treat the entire episode of acute respiratory distress. The user must time the dispensing shot of the hand-held nebulizer to coincide with a breath inspiration or the effect of the device is defeated and the medication shot is wasted. In contrast, a conventional nebulizer provides the ability for an acute respiratory sufferer to breathe as many times as needed to receive sufficient nebulized medication into the lungs to alleviate the acute distress symptoms. The conventional nebulizer thus does a different job as compared to the hand held inhaler.

In additional comparison, handheld inhalers typically contain numerous doses of medication while a conventional nebulizer contains no medication at all.

A critical problem solved by the present invention is that, while medication delivered by a conventional nebulizer could be more effective than medication delivered by a hand-held inhaler due to the availability of repeated inhalations of medication with the conventional nebulizer, there remains an important shortcoming, which is addressed by the inventive step of the current invention.

In order to use a conventional nebulizer it is necessary for a user, or someone assisting the user to (1) disassemble the nebulizer housing by removing its top so as to expose the nebulizing chamber; (2) locate a separately stored container of liquid medication to be nebulized; (3) carefully open the liquid medication container so as not to spill it; (4) pour the liquid medication directly into the nebulizing chamber without losing any of it through spilling into the nebulizer housing; (5) reassemble the nebulizer housing; and (6) position the inhaler mouthpiece in the mouth so as to inhale the nebulized medication.

A problem arises in that use of a nebulizer is not going to be sought until a person is already in acute respiratory distress. Otherwise, problems of nebulizer overuse, overmedication, medication side effects and a search for alternate pulmonary therapy modalities will all become concerns for a patient. Therefore, use of a conventional nebulizer implies that a user is experiencing acute pulmonary symptoms, is in acute distress, and is experiencing an emergency.

Persons suffering acute respiratory distress are routinely subject to being fearful, frightened, or fully panicked. Fear, fright and panic are well known to degrade performance on tasks requiring some level of skill in eye-hand coordination tasks. When seeking the use of a conventional nebulizer, then, a user is required to locate a separate container holding a dose of liquid medication, open the nebulizer, open the medication container, pour the liquid into the nebulizer chamber, and re-assemble the nebulizer housing. The aforedescribed sequence of steps can be difficult or impossible for a fearful, frightened or panicked sufferer of acute respiratory distress. An important consideration is that there will almost certainly be occasions when a person experiencing acute need of a conventional nebulizer is alone and without anyone to assist. It is just these occasions where a conventional nebulizer may be available but be impossible for a user to operate.

To solve the problem of user inability to operate a conventional nebulizer in an emergency, the present invention presents a simple solution: construct a conventional nebulizer than has a built-in stored dose of liquid medication and make that liquid dose injectable into the nebulizer chamber with either a simple twist of a screw cap or a single stroke of user force. As provided in the present invention the user will not be required to disassemble or reassemble the housing of a conventional nebulizer; will not be required to locate a separately stored container of liquid medication; will not be required to open the separate medication container; and will not be required to pour the liquid medication into the nebulizer chamber.

According to the present invention, a conventional nebulizer will have added to its housing a storage chamber, preferably cylindrical, for storing, in loaded-gun fashion, a dose of liquid medication on board the conventional nebulizer housing.

In one embodiment of the present invention, the novel storage chamber for the medication capsule is preferably a substantially cylindrical sleeve with an open top aperture projecting vertically downward from the inhaler pipe to a point slightly above the conventional nebulizer chamber within the housing of a conventional nebulizer. The sleeve's diameter is small enough so as not to interfere with the conventional nebulizer's free flow of air from the nebulizer chamber, up the conventional neck of a nebulizer and into the conventional inhaler pipe of a nebulizer. The medication capsule storage sleeve merely occupies a portion of the air passage between the nebulizer chamber and the inhaler pipe and thus in no way does the storage sleeve seal or impede the conventional free flow of air within what is otherwise a conventional nebulizer.

In one embodiment of the present invention the novel medication storage chamber is also sleeve-like; however, instead of extending vertically as does the sleeve of the preferred embodiment, the storage chamber of the non-preferred embodiment generally projects outwardly from an inner delivery end in proximity to the nebulizing chamber, through the wall of a conventional nebulizer housing, and extends to an outer user-access end.

In the non-preferred embodiment the novel structure medication storage chamber generally has a tapered-nozzle open-aperture delivery end disposed in close proximity to the nebulizing chamber so that the liquid medication, when deployed by a user, is injected reliably and directly into the nebulizing chamber.

In the present invention the novel medication storage chamber accepts a single disposable and user-replaceable capsule containing a dose of liquid medication to be nebulized in an emergency. The chamber is provided at its outer end with pressure means for a user to exert a stroke of physical force upon the outer end of the medication chamber so as to exert force or slicing against the medication cartridge. The capsule is generally cylindrical with an end sized to match and fit within the medication storage chamber. In one embodiment an outer end of the medication capsule is capable of accepting force from a manually-operated piston.

The medication dose capsule has a seal that is capable of rupture upon manual application of twisting or tearing pressure, the seal being located at an inner end of the capsule, disposed at or near the inner end of the medication storage chamber. The preferable emergency user-pressure means is a piston arrangement, where the piston is integral with the medication capsule, is elastomerically sealed, and accepts a push-force from a piston rod. The easily recognized example of this is a medical syringe.

In another embodiment, insertion of the medication capsule within a rotatable knob cam activation assembly facilities bursting of the seal of the medication reservoir capsule.

In a preferred embodiment, the medication capsule is opened by a sliding cutting blade activated by a plunger.

In the preferred embodiments, the cutter assembly is used with the angularly oriented blade, such as horizontally, vertically or obliquely oriented, which pierces the capsule when activated by a hand operated or automatically actuated plunger.

Therefore the novel combination of the present invention addresses and solves the problem of what procedure must be followed by a patient having a breathing emergency, such as a severe attack of asthma, and needs a quick reliable dose of nebulized medication, particular where (1) no other person is available to assist the patient and (2) a single-shot hand-held nebulizer is medically inappropriate for treatment.

DETAILED DESCRIPTION OF THE DRAWINGS

FIG. 1 is an exploded view of a prior art conventional nebulizer housing 10 shown disassembled. Conventional medication container 14 is shown adding liquid medication to conventional nebulizing chamber 15. In the event of a respiratory emergency, a user would have to locate a separate container of liquid medication 14, then open it, then disassemble (as shown) the portions of the nebulizer housing 10, then pour the liquid medication from its separate container 14 into nebulizer chamber 15, then reassemble nebulizer housing 10 before being able to inhale nebulized medication through proximal end of conventional mouthpiece 30 which is part of conventional breather 25, breather 25 having an open distal end 31 opposite to proximal end 30.

When a user has pour medication into nebulizer chamber 15 and reassembled housing 10, then conventional air supply line 20 supplies a stream of compressed air to nebulizer chamber 15 causing the liquid medication to become nebulized and urging the nebulized medication upward through connecting tube 11 so as to be available for user inhalation through proximal end mouthpiece 30.

FIG. 2 shows a perspective view of the prior art conventional nebulizer in use. A user inserts the proximal mouthpiece end 30 of breather 25 into the mouth and inhales. Nebulizer housing 10 [concealed by the user's hand in the drawing] furnishes nebulized (aerosolized) medication to the user for as many repeated inhalations as the user may need for alleviation of an acute respiratory emergency. Air supply lines 20 is shown extending upwardly but the user's hand conceals the intersection of air supply line 20 with the bottom of the nebulizer chamber 10.

In one embodiment of the present invention, the novel medication storage chamber generally projects outwardly from an inner delivery end in proximity to the nebulizing chamber, through the wall of a conventional nebulizer housing, and extends to an outer user-access end.

FIG. 3 shows a first embodiment of the present invention with a conventional nebulizer housing 10 fitted with novel integral (i.e., built-in) medication storage chamber 35. Storage chamber 35 is capable of receiving removable medication dose cartridge 40. Both chamber 35 and matching cartridge 40 are elongated, preferably cylindrical and both have matching inner and opposite outer ends. The inner end 36 of storage chamber 35 is disposed within nebulizer housing 10 while outer end 37 of chamber 35 is outside of nebulizer housing 10. Chamber 35 is fixed in a position that places its inner end 36 in close proximity to nebulizing chamber 15. The preferably cylindrical body of chamber 35 points radially outward from nebulizing chamber 15 so that outer end 37 of medication storage chamber 35 is outside of and spaced apart from nebulizer housing 10.

Medication storage chamber 35 is provided with open-ended tapered nozzle 38 at its inner end 36, nozzle 38 being in close proximity to nebulizing chamber 15 so as to reliably inject a dose of liquid medication from cartridge 40 upon user application of a single inwardly directed pressure stroke to pressure plate 56 of grooved piston rod 50, disposed within medication storage chamber 35, at the outer end 37 of said storage chamber.

Medication cartridge 40 is provided with tapered inner end 42 tapered to open end 45. Pressure seal 43 is located at inner end 42 of cartridge 40 while elastomerically sealed piston 44 is located at the outer end of cartridge 44. Upon user application of a single stroke of inward pressure on pressure plate 56 at the outer end of piston rod 50 (user grasps Finger Engagements Wings 52 for convenience), contact is made between grooved piston rod 50 and piston 44 resulting in an increase in hydraulic pressure on seal 43. Tapered shoulders 47 of cartridge 40 contact and engage tapered nozzle 38 of medication storage chamber 35, causing cartridge 40 to become seated firmly within cartridge 35 when a user applies manual pressure to pressure plate 56 of grooved piston rod 50.

Seal 43 is manufactured so as to burst upon user force application on pressure plate 56 of grooved piston rod 50. When seal 43 bursts, pressure from grooved piston rod 50 causes injection of liquid medication from cartridge 40 into nebulizing chamber 15. The remainder of the nebulizing operation is conventional.

FIG. 4 shows the first embodiment of the present invention with a detail of removable medication dose cartridge 40, having pressure seal 43 disposed at inner end 42, open end 45 is comprised of the tapered shoulders 47 at inner end 42 of cartridge 40 and outer end 41 contains movable elastomerically sealed piston 44. Piston 44 receives pressure from grooved piston rod 50. In response, piston 44 moves in an inward direction applying hydraulic pressure to the liquid medication contained within the body of cartridge 40. In turn the hydraulic pressure causes seal 43 at the inner end of cartridge 40 to burst. When seal 43 ruptures, liquid medication is forced under piston pressure to be injected into nebulizing chamber 15. FIG. 5 shows the first embodiment of the present invention with a cut away side view detail of medication storage chamber 35 intersecting nebulizer housing 10 so as to have inner end 36 of chamber 35 in close proximity to nebulizing chamber 15 for reliable injection into chamber 15 of liquid medication from open inner end 43 of cartridge 40 upon application of a single stroke of inward user pressure upon pressure plate 56 of grooved piston rod 50, the force being transmitted to piston 44 of cartridge 40. Stop 55 engages groove on piston rod 50, preventing piston rod 50 from coming out of medication storage chamber 35.

As shown in a second alternate embodiment shown in FIGS. 6 and 7, the is novel medication storage sleeve 62 projects vertically downward from the top of horizontal inhaling pipe 70 extending downwardly into the nebulizer housing 10 to a point just above the nebulizing chamber 15. A medication dose capsule 66 is an elongated substantially cylindrical container oriented vertically within sleeve 62.

Capsule 66 is user inserted and user removed respectively to and from sleeve 62. Capsule 66 is intended to be stored in sleeve 66 until used, and then removed and replaced in preparation for a next use of the nebulizer.

Capsule 66 has a lower end tear off tab 64. Sleeve 62 has lower end stop means 62c to engage tear off tab 64 to prevent tab 64 from turning when torque is applied to capsule 66. Stop means 62a is attached by a retention means, such as bracket 62b, within hollow sleeve 62, allowing fluid flow of the liquid medication through lots 62a and 62b and then through aperture 62d of hollow sleeve 62.

Sleeve 62 accepts screw cap activating handle 68 after a user inserts capsule 66 into sleeve 62. Screw cap 68 engages projection means on capsule 66 so as to twist capsule 66 within sleeve 62 when a user applies a torque force to screw cap 68. Because the lower end tear off tab 64 of capsule 66 is prevented from twisting by the stop means 62a within sleeve 66, capsule 66 is caused to shear and rupture at its lower end when a user twists cap 68.

After capsule 66 is opened by twist off of tear off tab 64, capsule 66 is subject to squeezing compression by a capsule squeezer, such as a can activator or other crushing device known to those skilled in the art. Liquid medication within capsule 66 flows by gravity into nebulizing chamber 15 upon rupture of the lower end of capsule 66. The liquid medication is then conventionally nebulized and the user gets the therapeutic benefit of the nebulizer in a conventional manner.

FIG. 6 shows an exploded view of the second embodiment for the novel medication storage sleeve 62 projects vertically downward from the top of horizontal inhaling pipe 70 extending downwardly into the nebulizer housing 10 to a point just above the nebulizing chamber 15. A medication dose capsule 66 is an elongated substantially cylindrical container oriented vertically within sleeve 62.

Capsule 66 is user inserted and user removed respectively to and from sleeve 62. Capsule 66 is intended to be stored in sleeve 66 until used, and then removed and replaced in preparation for a next use of the nebulizer.

Capsule 66 has a lower end tear off tab 64. Sleeve 66 has lower end stop means to engage tear off tab 64 to prevent tab 64 from turning when torque is applied to capsule 66

Sleeve 62 accepts screw cap activating handle 68 after a user inserts capsule 66 into sleeve 62. Screw cap 68 engages projection means on capsule 66 so as to twist capsule 66 within sleeve 62 when a user applies a torque force to screw cap 68. Because the lower end tear off tab 64 of capsule 66 is prevented from twisting by the stop means within sleeve 66, capsule 66 is caused to shear and rupture at its lower end when a user twists cap 68. Liquid medication within capsule 66 flows by gravity into nebulizing chamber 15 upon rupture of the lower end of capsule 66. The liquid medication is then conventionally nebulized and the user gets the therapeutic benefit of the nebulizer in a conventional manner.

FIG. 7 shows a detailed perspective of the second embodiment of the present invention. A user applies torque to screw cap 68 which in turn applies torque to medication capsule 66 seated within storage sleeve 62. Stop means 62c engages tear off tab 64 so that applied torque causes rupture of capsule 66, allowing its contents to flow by gravity into conventional nebulizer chamber 15.

FIG. 8 shows the third embodiment, having a vertical storage sleeve 62 for a capsule 66 of liquid medication, where the capsule 66 is seated with its tear-off tab 64 in close proximity to the conventional nebulizing chamber within the housing of the conventional nebulizer. FIGS. 9, 10 and 11 show a vertical storage sleeve 62 of the third embodiment for the capsule 66 of liquid medication, showing a lever 69 actuating lever arm 69a, which exerts pressure against lever arm paddle 69b against capsule 66, thereby moving the capsule 66 laterally, while the tear-off portion 64 of the capsule is seated and immobilized within stop means 62c, so that lateral pushing of the capsule 66 causes a tear of the capsule 66 at the tear-off portion 64 and fluid flow through slots 62a and 62b adjacent to stop means 62c, through aperture 62d and into the fluid reservoir portion 15 of the nebulizer.

FIGS. 12-16 show a fourth alternate embodiment for a knob cam assembly for bursting the tear off tab 64 from capsule 66. As shown in FIG. 12, capsule 66 is inserted through a port in knob activator 168 between capsule pincher blades 180a and 180b, down to restraining stop means 162c, adjacent to one or more mist ports 162a and/or 162b, etc., which, after bursting of the seal between capsule 66 and tear off tab 68, medication is misted within nebulizer 14 upward to inhaling pipe 70 and mouthpiece 30. Ports 162a and/or 162b, as well as restraining stop means 162c are down stream of inhaling pipe 70, between nebulizer 14 and inhaling pipe 70.

Rotation of knob activator 168 causes twisting of capsule 66 between capsule pincher blades 180a and 180b, and thence against cam contact protrusion elements 192a and 192b of cam assembly 190, which rotates in unison with rotation of knob activator 168, while restraining stop means holds tear off tab 64 of capsule 66 during rotation of capsule 66 within cam assembly 190.

Rotation of knob activator 168 and cam assembly 190 is limited to a preferable arc of movement, such as, for example 180 degrees, by means of reciprocating stop element 194a on inhalation pipe 70 being stopped by reciprocating stop element 194b on the adjacent bottom of cam assembly 190.

FIGS. 17-48B show alternate embodiments where the medication capsule is severed by a blade at an appropriate wide portion so that ambient air pressure is not a factor, so the capsule does not need to be opened and crushed to insure fluid flow through the narrow discharge end of the capsule, as shown in FIGS. 13-16.

FIG. 17 shows the major components of a fifth embodiment of a nebulizer assembly 200 of the present invention, where the medication capsule 300 is opened by being severed with a cutting blade 270. Nebulizer assembly 200 has a vertical storage chamber 210 for containing medication dosage capsule 300 in a ready position for use by pressing on finger grip 280 of blade plunger assembly 260 urging flat blade plunger 265 within hollow flat blade plunger guide 250. Drainage weep holes 292 for cleaning purposes are covered by removable cap 295.

Cutting blade 270 with sharpened angled leading edge is shown in the top view of blade plunger assembly 260 in FIG. 18. Note plunger flow aperture 275 which provides an unobstructed flow region for medication to flow out of capsule 300 after it is cut. Fixed finger grip 255 provides a convenient surface for a compression action using thumb and fingers of one hand to perform the cutting motion. Note that after capsule 300 is inserted into chamber 210 in ready storage for the next asthma episode, cap 290 is used to seal the large opening 210a at the top of chamber 210. Cap 290 keeps capsule 300 from jumping out of after being sliced and cut. Note that after cutting, medicine will flow down into conventional nebulizing chamber 240 wherein it is broken up into fine droplets by action of compressed air being fed in from the bottom. Inhalation tube 220 with mouthpiece 230 complete the major portions of nebulizer 200.

FIGS. 19 through 22 are crossectional detail views of the progression of the cutting operation of medication dosage capsule 300 at its necked down distal end 300a.

In FIG. 19, blade 270 is spaced away from capsule 300; this is the normal storage position.

FIG. 20 shows blade 270 approaching the side of capsule 300 to be severed. In FIG. 21, blade 270 is in first contact with the side of capsule 300.

FIG. 22 shows the situation just after capsule 300 is cut with medication flowing out through plunger flow aperture 275 and from severed end 300a.

FIG. 23 shows the entire nebulizer system including air compressor housing 310 which is connected to nebulizer 240 via compressed air tubing 330. Also shown is fixed finger grip 555 attached to hollow plunger guide 550 for slidable insertion of blade assembly 560, shown in FIG. 24. Fixed finger grip 555 provides a convenient surface for a compression action using the fingers and hand to perform the cutting motion.

Figure 25A:
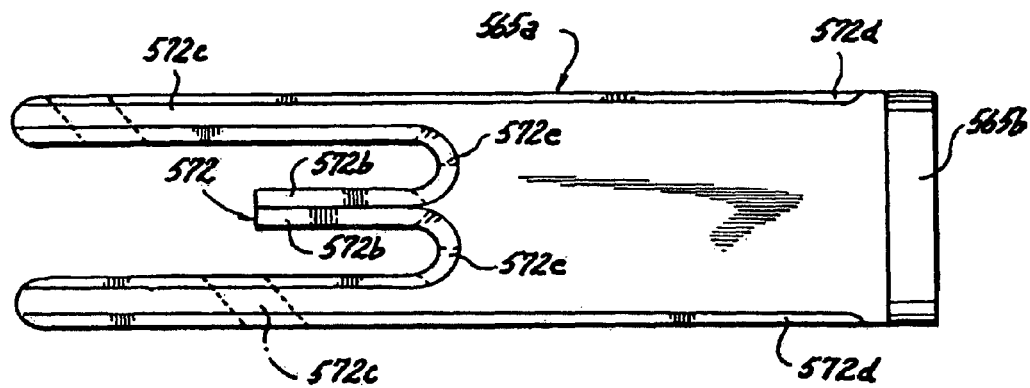
FIG. 25A is a top plan view of an alternate embodiment for a blade plunger.
Figure 25B:
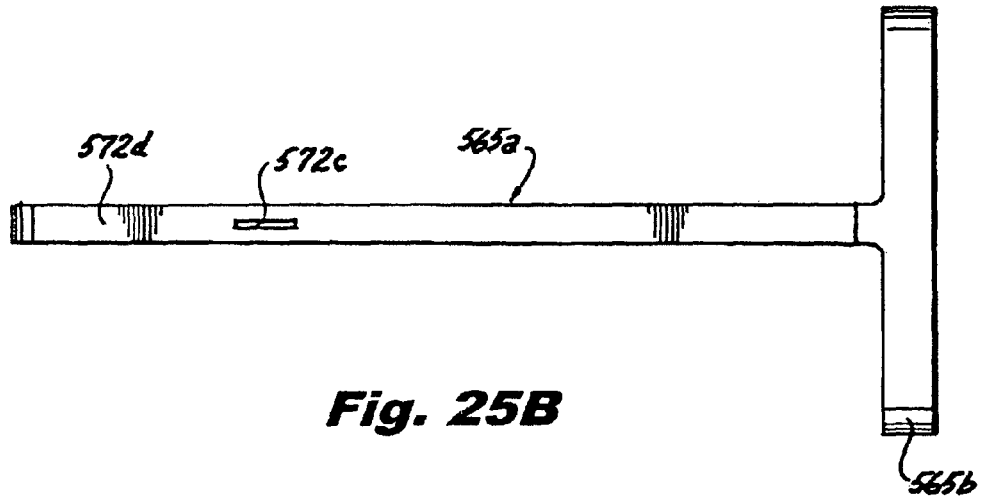
FIG. 25B is a side elevational view thereof.
Figure 25C:
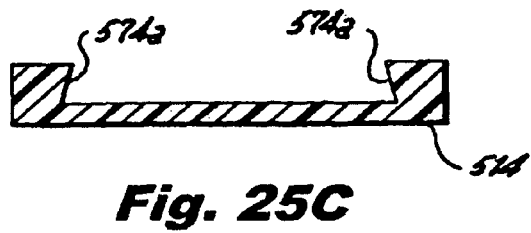
FIG. 25C is a crossectional view of a bottom portion of a blade plunger guide for the blade plunger of FIG. 25A.
Figure 26:
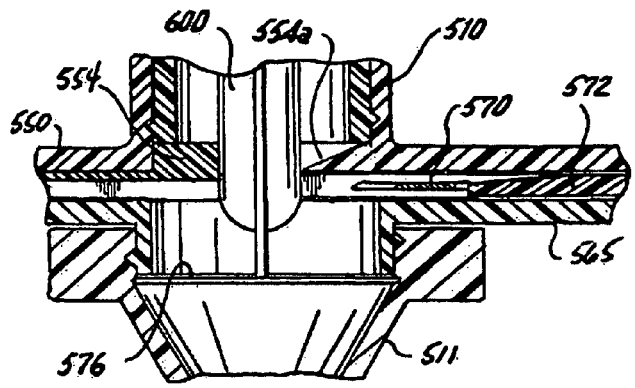
FIGS. 26, 27 and 28 are a sequence of three side crossectional detail views showing the progress of the cutting blade from right to left in cutting through the medication dosage capsule and the release of the medication downward toward the nebulizer chamber.
Figure 26A:
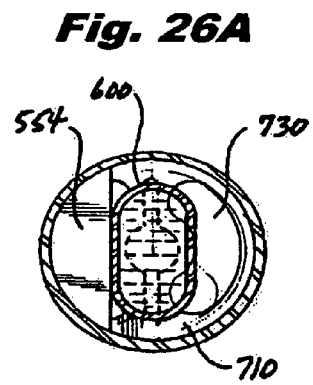
FIG. 26A is a close-up top plan view of the capsule support region.
Figure 27:
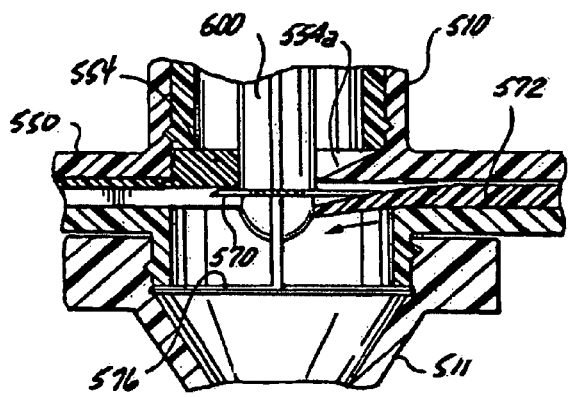
Figure 28:
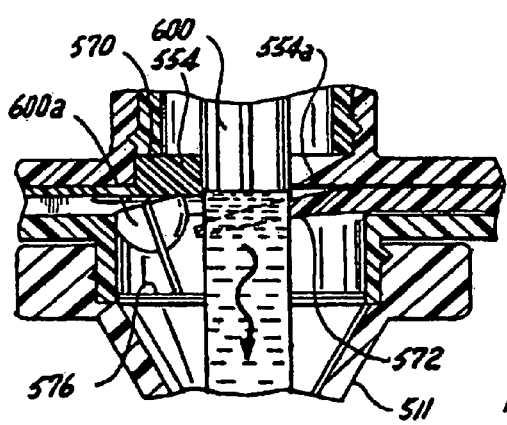

FIGS. 24-28 show the major components of the sixth alternate embodiment of a nebulizer assembly 500 of the present invention, where the medication capsule 600 is opened by being severed with a cutting blade 570 (see FIG. 24). As shown in FIGS. 26-28, the nebulizer assembly has a vertical storage chamber 510 for containing medication dosage capsule 600 in a ready position for use by pressing on hand grip 580 of blade plunger assembly 560, urging flat blade plunger 565 within hollow pocket 551 of flat blade plunger guide 550, as shown in FIG. 23.

As shown in FIG. 24, cutting blade 570 with sharpened angled leading edge (approximately 25-65 degrees, preferably 45 degrees) is shown in the perspective view of blade plunger assembly 560. FIG. 24 also shows rigid or slightly flexible follower paddle 572 with adjacent fluid flow opening 573. Follower paddle 572 pushes severed distal portion 600a out of the way as shown in FIG. 28, in preloadable chamber medication capsule storage region 510, which is located above upper platform 710, which, in turn, is located above fluid transport chamber 511. Fluid transport chamber 511 is preferably acute tunnel-shaped in configuration, for optional fluid flow of fluid, past inhalation tube 220, directly into conventional nebulizing chamber 240.

As shown in FIG. 24A, in order to assure the correct orientation of blade plunger guide 550 of blade plunger assembly 560, when, inserted into hollow pocket 551 thereof, blade plunger 565 has linear tongue 552 insertable within linear groove 553 of an inside wall of blade plunger guide 550. While tongue 552 is v-shaped, alternatively it can be a single oblique edge sliding against a corresponding oblique edge, such as shown in FIG. 25C.

FIGS. 24B, 24C and 24D show another embodiment for an orientation sub-assembly for the blade plunger assembly 560. Blade plunger 565 includes a misorientation stop protrusion button 552a, which is slidably insertable within linear groove 553a within an inner top surface of blade plunger guide 550 when blade plunger 565 is correctly oriented for insertion within blade plunger assembly 550. External misorientation stop 552b is provided extending axially outward from a bottom portion of blade plunger assembly 550, to contact misorientation stop protrusion button 552a if blade plunger 565 is not correctly positioned for insertion.

FIG. 24C is a close-up front elevational view of the plunger portion thereof;

FIG. 24D is a top plan view of the plunger guide of the orientation sub-assembly of FIG. 24B;

FIG. 25 shows a detail of follower paddle 572 showing its sloping upper surface, sloping downward from an axially extending, centered imaginary line, preferably the leading edge of paddle follower 572 is flat to facilitate positive contact with severed capsule portion 600a. When viewed at the distal end, follower paddle 572 therefore has a generally axially extending triangular crossection. The paddle follower 572 is used to separate the cut capsule 600, 600a to insure that all liquid is able to drain into conventional nebulizer misting chamber 240. Follower paddle 572 is significantly smaller in area than surrounding opening 573 behind blade 570, to enhance fluid flow therethrough when pushing severed distal portion 600a out of the way. The rounded neck of follower paddle 572, as indicated by the curvature arrow, is preferably smaller in width than a crossectional area of cut capsule 600.

FIGS. 25A, 25B and 25C, show an alternate preferred embodiment for a cutter, including blade plunger 565a having finger/hand grip 565b and slots 572c for cutting blade 570. Blade plunger 565a includes blade follower paddle 572, which is generally triangular in crossection, including slanted sides 572b converging at an axially extending apex thereof. Outer lateral edges 572*d* are slanted to insure proper orientation of blade plunger 565*a* within slanted walls 574*a* of a bottom portion of optional blade plunger guide 574. Follower paddle 572 extends axially forward from inner edge 572 of preferred optional blade plunger 565*a*.

FIGS. 26 through 28 are crossectional detail views of the sixth embodiment, showing the progression of the cutting operation of medication dosage capsule 600 at its distal end 600*a*, and the pushing of severed distal portion 600*a* out of the way above screen 576.

In FIGS. 26 and 26A, blade 570 is spaced away from capsule 600; this is the normal storage position. Capsule 600 is preloaded to rest against capsule stabilizer block 554, which facilitates clean slicing of capsule 600. Capsule stabilizer block 554 is located above capsule base holder 710. Additionally sloping capsule guide 554*a* is provided juxtaposed on an opposite side of vertical storage chamber 510 so capsule 600 does not lodge by mistake into one of the peripheral holes 730 in platform 710, but rather is correctly guided and nested into central hole 720. Sloping capsule guide 554*a* also assists in sliding the severed capsule 600 out of the way.

In FIG. 27, blade 570 has cut through capsule 600.

FIG. 28 shows the situation just after capsule 600 is cut with medication flowing around follower paddle 522, out through plunger flow aperture 573 behind blade 570 and through discharge tube 575. Follower paddle 572 pushes severed distal portion 600*a* out of the way, within chamber medication capsule storage region 510. To insure separation of the cut portions of medication capsule 600 by the leading edge of follower paddle 572, the rounded top surface is angled downward so that the contact region of follower paddle 572 with cut end 600*a* is below the level of blade 570.

FIGS. 29-33 show the seventh embodiment of nebulizer with improved medication capsule holding features for easier cutting action.

FIG. 29 also shows an alternate design for medication capsule 700 which is wider and flatter, for example, than capsule 600 with a pointed top end 705. A modified base holder 710 has a central hole 720 with extending slots 722 which can accept a wide range of capsule designs. A capsule type 600 is held with the bottom end partially within hole 720, while a capsule of type 700 is held above hole 720 with flat end engaged within radially extending slots 722 as shown in the detail of FIG. 29. Since capsules 600 or 700 are soft in their midsection, blade cuts thereof should be close to a bottom portion thereof, so that a clean cut occurs to insure maximum emptying of fluid contents therefrom. However, the blade cut must be through the hollow fluid filled portion, not through the solid tear-off portion of capsule 600 or 700.

Other features which enhance the holding action are housed within storage chamber cap 590 having an opaque bottom portion 590*a* and a light transmissive transparent or translucent top portion, as shown in FIG. 30. These include coil spring 750 which is used to press down on the top end of either style of medication capsule. Fixed spring retainer 740 engages the top distal end of coil spring 750 and retains it in a fixed position at the inside top of cap 590. Bottom collar 760 engages the bottom end of coil spring 750 and slides freely (as a piston) on the inside surface of cap 590. Attached to collar 760 is a conical top medication capsule holder 770 which will center either the flat top and bottom ends of capsule 600 or the pointed top end 705 or flat bottom end 706 of capsule 700. The bottom portion 590*a* of cap 590 is preferably opaque, to conceal bottom collar 760 from view when no medication capsule 600 is present underneath conical top medication capsule holder 770. However, when a medication capsule 600 is present, it exerts upward pushing pressure against conical medication capsule holder 770 and spring 750, thereby raising bottom collar 760 upward so that it is viewable through the upper transparent or translucent portion of storage chamber cap 590, above opaque bottom portion 590*a*. Additionally, to assist the user in viewing bottom collar 760, to view the presence of a medication capsule, bottom collar 760 preferably has visually perceptible indicia 760*a* thereon.

FIG. 32 shows the inner alignment of the components of the storage chamber. Note that spring 750 is compressed by the presence of either capsule is 700 (as shown) or 600. This is a view just prior to blade 570 approaching the side of capsule 700. FIG. 33 is a snapshot view just after cutting of medication capsule 600 showing medication flowing through central hole 720 and peripheral holes 730 into the chamber below.

FIGS. 34-37 show an eighth alternate embodiment for a fully integrated system for turning on compressor motor 410 of compressor 420.

FIGS. 34-36 show integrated air compressor housing 311 connected to nebulizer 200 via compressed air tubing 330. Also shown is plunger switch 360 centrally mounted on fixed finger grip 555 and attached to compressor housing 311 via cable 365. Optional connector 365*a* on cable 365 is used to permit the nebulizer portion to be more conveniently disconnected from the compressor for convenient cleaning and sanitizing. Switch 360 is preferably a 2 Button "rocker" switch left in "OFF" for stand by to use. Optionally, it can be a magnetic switch or other automated switch. Switch 360 is activated by movement of plunger hand grip 580 against "ON" contact button 370, which is mounted on a lower portion of grip 555. Switch 360 is a waterproof switch, such as, for example, a 2-wire, maintained contact 2 Button "rocker", such as provided by Control Products, Inc. in their K5000 Series industrial waterproof switches. "OFF" switch button 370*a*, located below "ON" switch button 370, turns off the circuit and puts the system back to "stand by" status. It can be re-energized by pressing manual compressor switch button 340 or by re-activating plunger assembly 560, causing contact of hand grip 580 against "ON" switch button 370 of switch 360 located on fixed finger grip 555. In an alternate embodiment, an indicator light 365*b* is added to indicate standby mode. This is the mode wherein connector 365*a* is engaged, power is on, but switch 360 is in the OFF position. Although any light emitter compatible with available voltage can be used, the preferred device is a green light emitting diode (LED).

FIG. 35 shows these two parts, fixed hand grip 580 and "ON" switch button 370 of switch 360 contacting each other upon actuation. "OFF" button 370*a* is used to turn off switch 360. When "ON" button 370 is pressed, the contact is closed. When "OFF" button 370*a* is pressed in, the contact is open. Preferably, optional resilient contact button bumper 580*a* insures contact between fixed hand grip 580 and "ON" button 370. In operation, nebulizer 200 would be stored with medication dosage capsule 300, 600 or 700 stored in ready orientation in chamber 210. Compressor wall plug 320 would be normally energized in an AC power source outlet. Manual override button 340, only necessary in case of failure of switch 360, or any part of the circuit would be in the "OFF" position. In a usage situation (possibly in the throes of an asthma attack), the user need only press plunger hand grip 580 toward fixed finger grip 555, activating "ON" button 370 of switch 360, thereby cutting capsule 300 emptying medication into conventional nebulizing chamber 240 and then inhaling through mouthpiece 230. The action of cutting capsule 300 simultaneously switches on the compressor without use of manual switch 340 on compressor housing 311. The system is a fault tolerant system, wherein if the circuit fails, override button 340 will complete the circuit directly to motor 410, bypassing contacts 395 of relay 380 thereby operating regardless of multiple failures of switch 360, cable 365 or relay 380.

A locator light emitting indicator outlet 313 is optional to put a "night light" 315 therein. Outlet 313 is always "ON". Holder 314 has a slot for engaging the end of flat blade plunger guide 250 as well as a partial round cutout to accommodate the curvature of cap 290, for easy storage of nebulizer opening assembly and inhaler therein.

Figure 37:
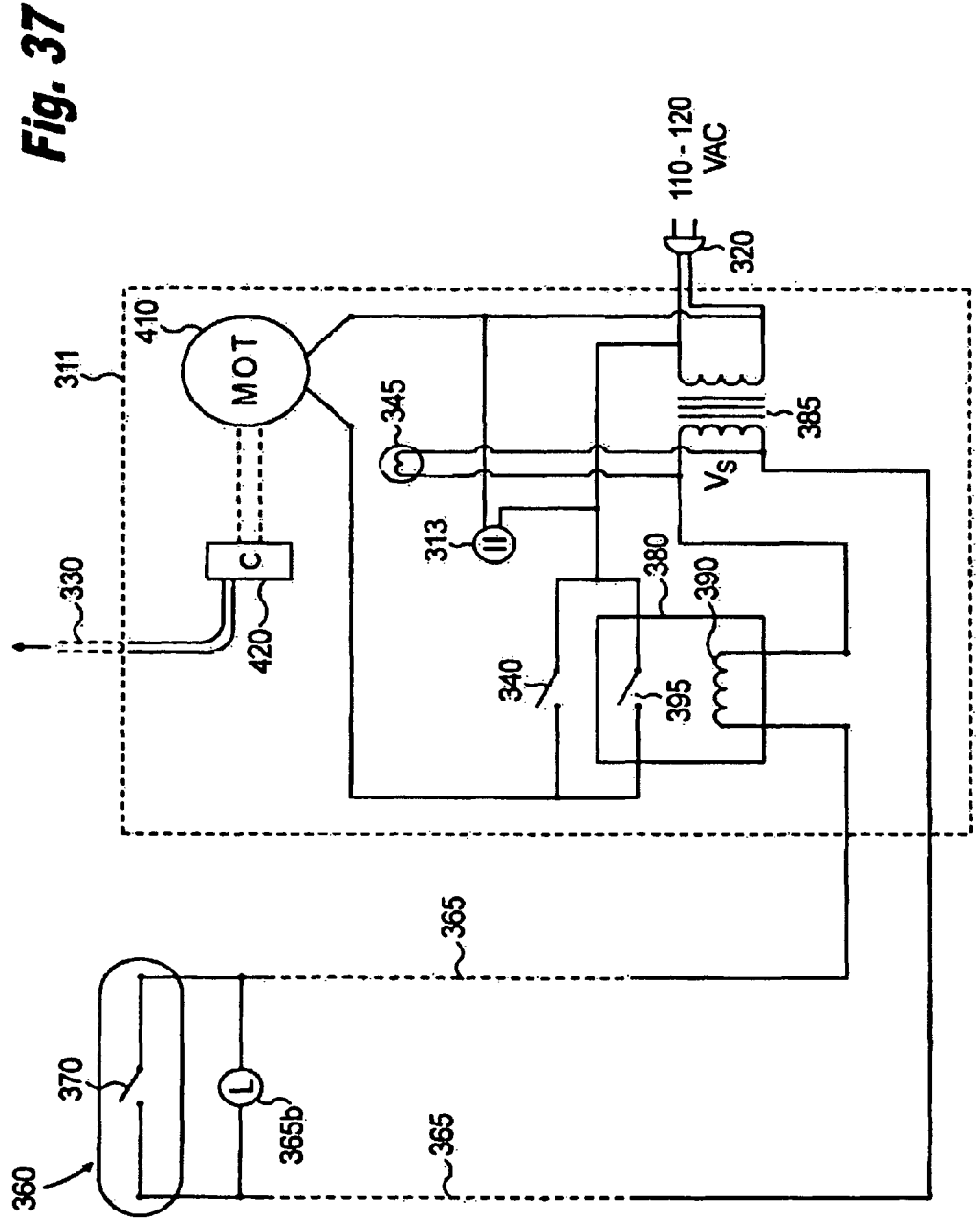

The schematic diagram of FIG. 37 explains the operation and shows the physical location of major components shown in FIGS. 34-36 since dashed line 311, in the schematic diagram of FIG. 37, shows the boundary of compressor housing 311. Transformer 385 supplies a low voltage Vs (typically a safe 12 or 24 volts) to operate relay 380 and indicator lamp 345 which is always on as an indicator that transformer 385 is operating on stand by energize relay coil 390 when switch 360 is on and the circuit is complete. Note that actuation of switch 360 by action of ON button 370 would provide voltage Vs to relay coil 390 thereby causing normally open relay contacts 395 to close thereby energizing compressor motor 410. In the unlikely event that operation is not initiated by attempted actuation of switch 360, manual switch 340 on compressor housing 311 can be used to initiate operation since it is wired directly to motor 410. Note that transformer 385 is continuously energized as long as plug 320 is plugged-in so that the entire nebulizer system is in a quick-ready mode of operation at all times. Compressor 420 is driven by motor 410 to supply air pressure to nebulizing chamber 240 to atomize medication in a mist to the patient.

Figure 38:
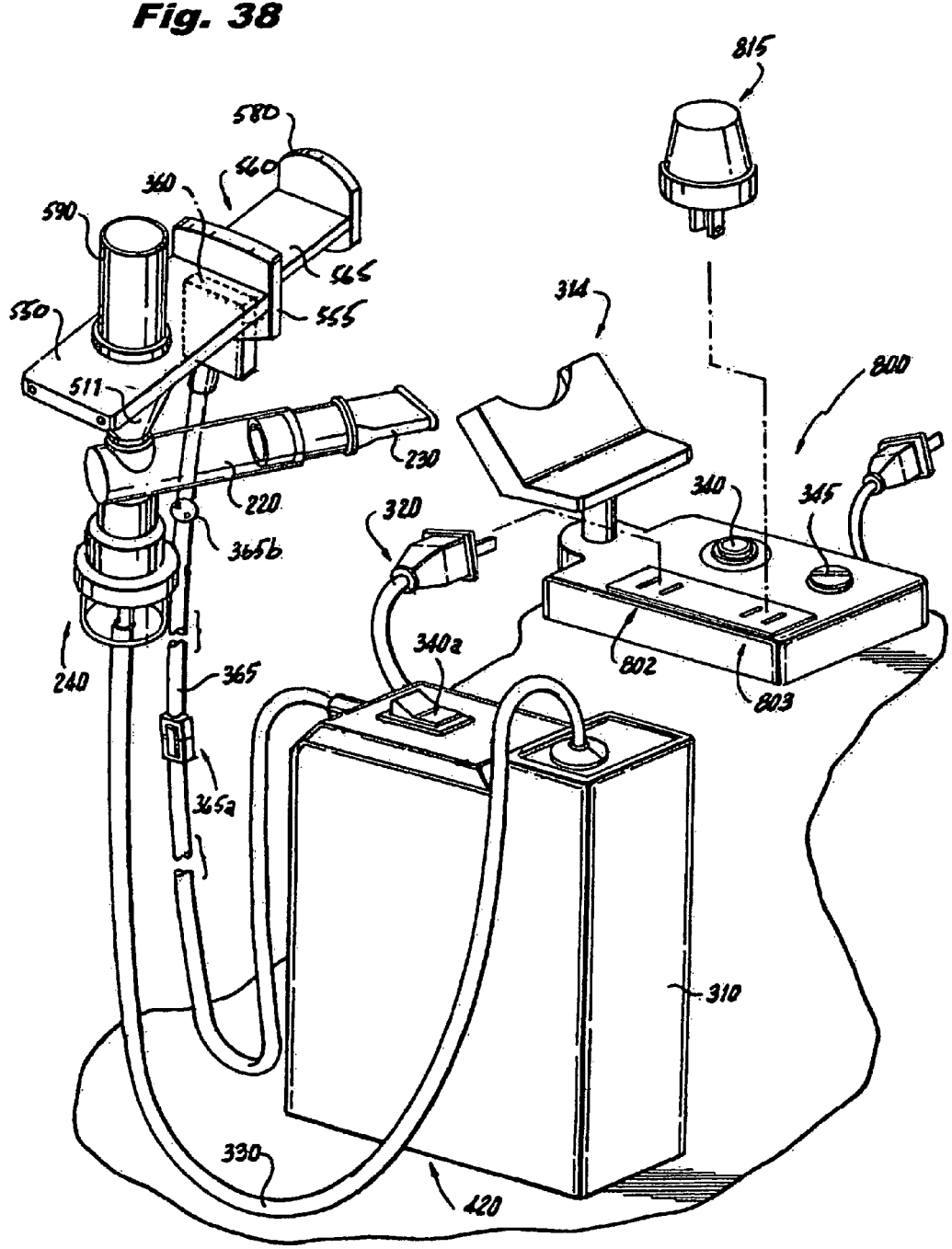
FIG. 38 shows an auxiliary plug-in, not integrated starter box for automatically starting the misting compressor of the nebulizer inhaler of FIG. 17.

FIG. 38 shows a ninth embodiment for an auxiliary plug-in starting box 800 for automatically starting the misting compressor motor 410 of a conventional compressor housing 310 of the nebulizer inhaler. This embodiment is a retrofit for a conventional compressor subassembly.

Figure 39:
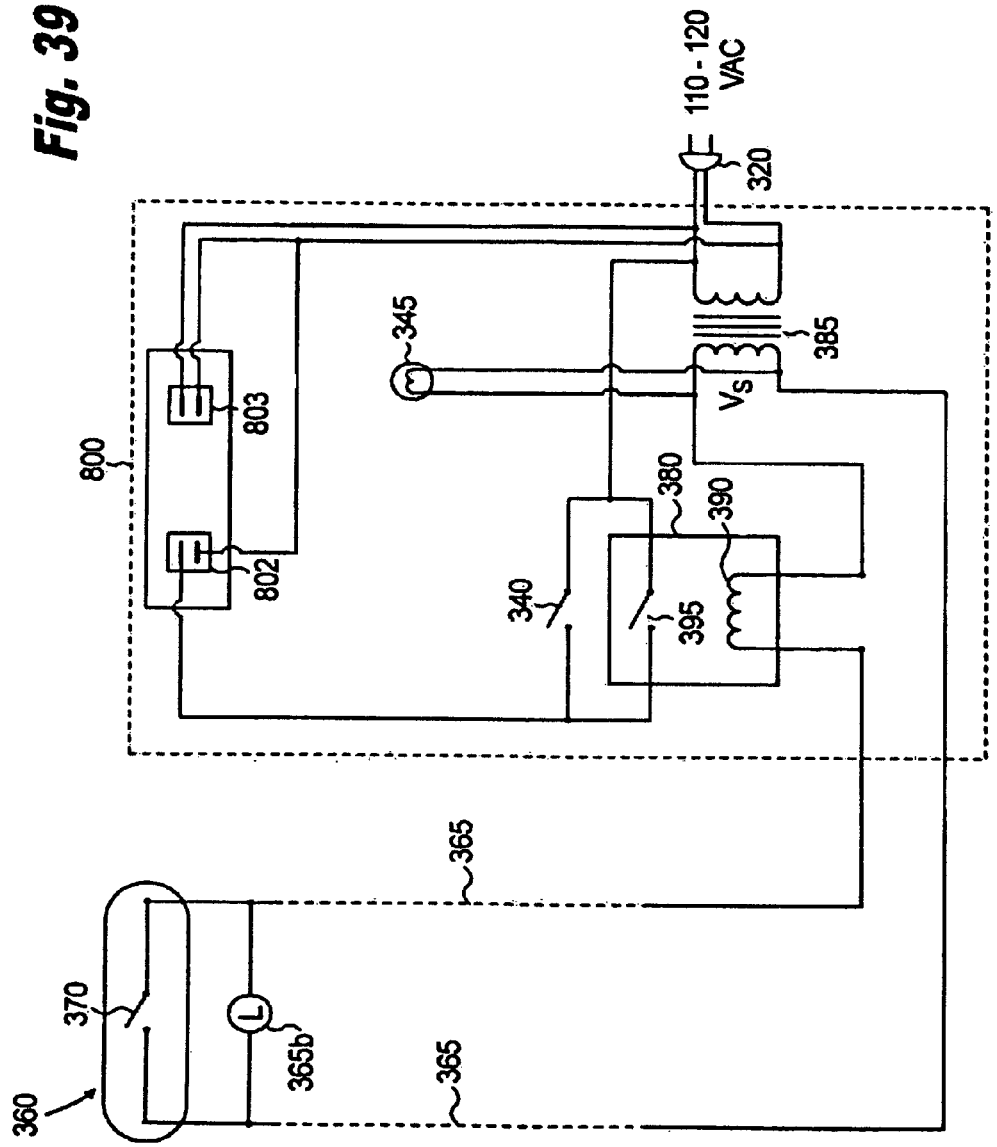
FIG. 39 is a schematic diagram thereof.

FIG. 39 is an electrical schematic diagram thereof. One outlet 802 is provided for inserting the plug 320 from the nebulizer compressor motor 410. The other outlet 803 is for a user insertable plug for a night light 815, to provide visual access in the dark. The backup emergency press button 340a will start the nebulizer compressor motor 410 of conventional compressor housing 310 of FIG. 38 if the plunger 560 does not work. Green indicator light 345 indicates that the transformer 385 for the compressor is "ON." Nebulizer holder 314 is provided to hold plunger guide 550 therein. Plunger assembly 550 also includes switch 360 with "ON" switch button 370 and "OFF" button 370a such as is shown in FIGS. 35 and 36 and applicable herein. Switch 360 is activated upon contact of button 370 by hand grip 580. Nebulizer plug 320 is energized when either switch 360 or switch 340a is closed. The system is a fault tolerant system—if the circuit fails, compressor manual switch 340a is available to activate.

Two motor powered blade plunger subassembly versions as well as a relay-type control system are described in FIGS. 40-44.

Figure 40:
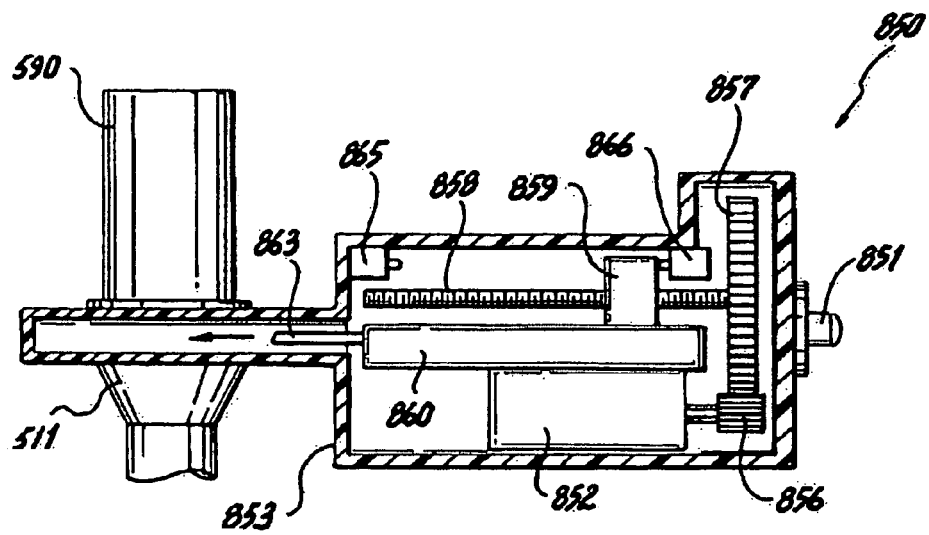
FIG. 40 is a side elevation of a lead screw type powered blade plunger with the housing shown in crossection.
Figure 41:
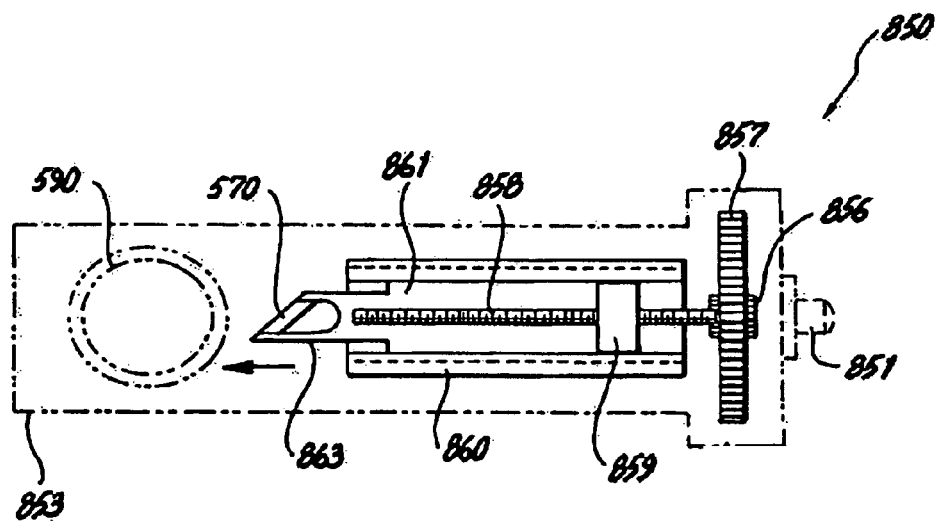
FIG. 41 is a top view of the motion elements of the embodiment of FIG. 40.

FIG. 40 is a side view of lead screw version 850. Within housing 853 is DCPM motor 852 with output shaft gear 856 which is meshed with gear 857 driving lead screw 858. Lead screw nut 859 is attached to a carriage plate 861 (see FIG. 41 for a top view) which rides in side grooves of linear guide 860. The front end of plate 861 is formed into holder 863 of blade 570. Limit switches 865 and 866 detect the permissible limits of travel of carriage plate 861. Momentary or other "on/off" contact pushbutton 851 starts the automatic medication container cutting procedure.

Figure 42:
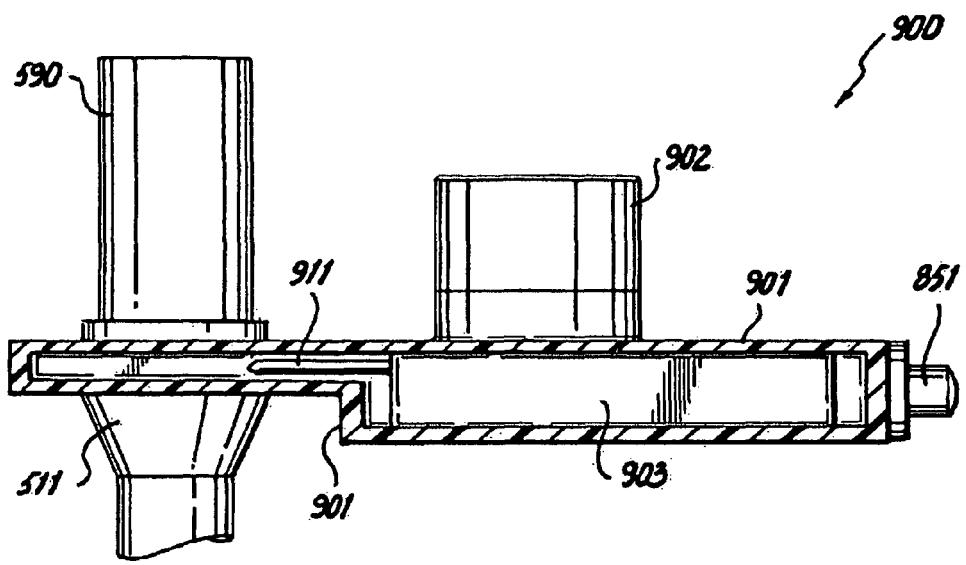
FIG. 42 is a side elevation of a rack and pinion type powered blade plunger shown with the housing shown in crossection.
Figure 43:
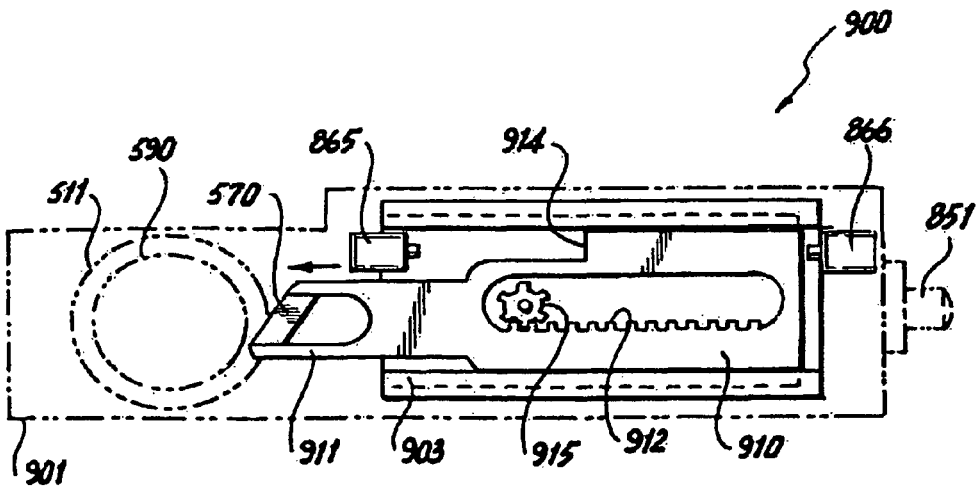
FIG. 43 is a bottom view of the motion components of the embodiment of FIG. 42.

Side view FIG. 42 and bottom view FIG. 43 show details of an alternate implementation of powered blade plunger 900 using a rack and pinion mechanism instead of a lead screw. A low output speed gearmotor 902 preferably incorporating a DCPM design powers the elements within housing 901. Grooved linear guide 903 guides carriage plate 910 with rack gear teeth 912 engaging motor pinion gear 915. The front end of plate 910 is formed into holder 911 for blade 570. Edge 914 engages limit switch 865 on its forward excursion initiating an automatic reversal of motor 902.

Figure 44:
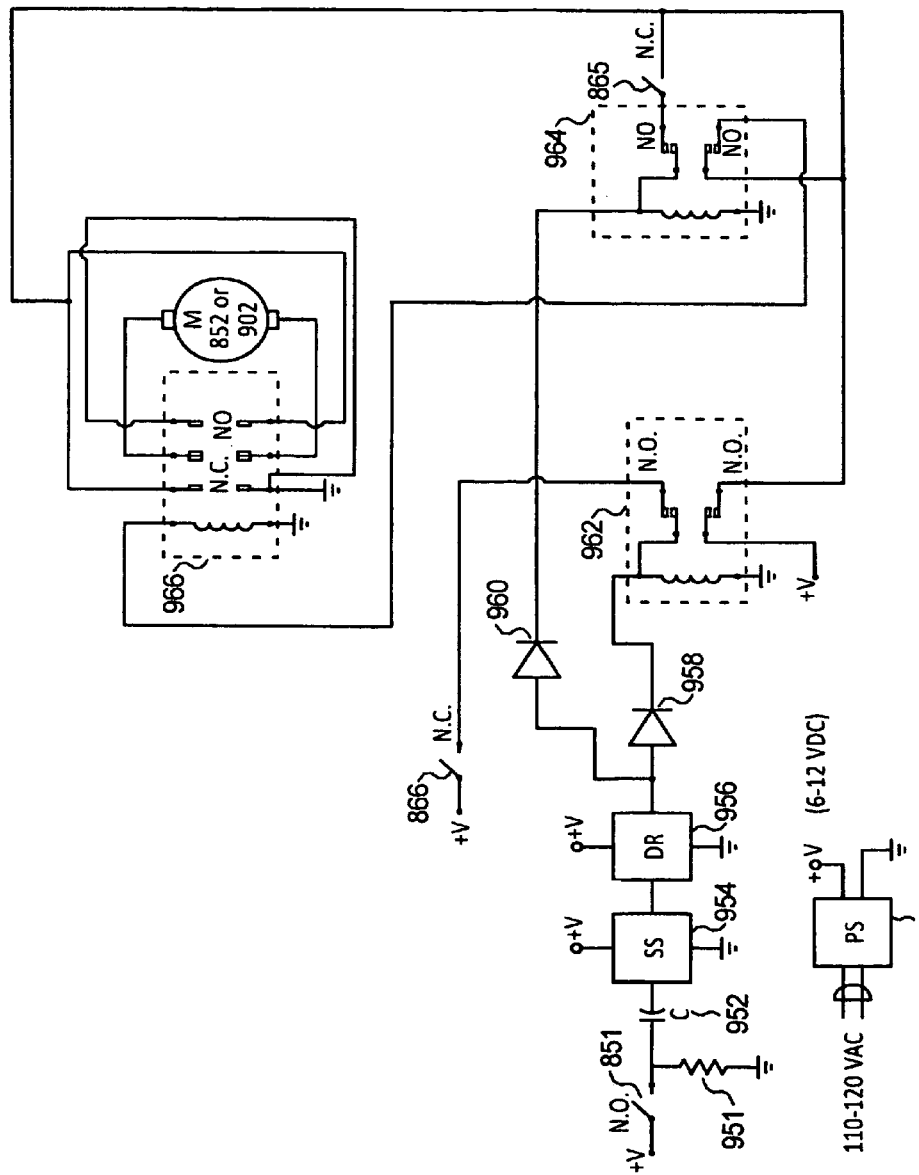
FIG. 44 is a schematic diagram of a control circuit for either type of powered blade implementation using three relays and a other components.

The control system for either implementation of powered blade plunger is described by the control circuit of FIG. 44. This circuit can be stand-alone, or it can be integrated with the systems described in the schematic diagrams of FIGS. 37 and 39.

Power supply 950 supplies a low DC voltage (e.g. –6 to 12 volts) compatible with the relays and motor used. Pushbutton 851 is normally open. When pressed it supplies a short voltage pulse through capacitor 952 (typically 0.05 ufd) which triggers the start of a timed output pulse from single-shot timer block 954 (about 40-80 ms). Resistor 951 (typically 500 k-ohms) simply bleeds off capacitor 952. Blocking diodes 958 and 960 permit the use of a single relay driver 956 to drive two separate relays with feedback isolation. Relay 962 with two double pole single throw contact pairs controls voltage applied to the motor and to a control relay 964 (same type) which initiates motor reversal at the limit point after the medicine capsule is severed. Relays 962 and 964 each use one set of contacts to latch up the relays after they are initially turned on by driver 956. Relay 966 has a two pole-double throw configuration of contacts with both normally closed and normally open contact pairs; this relay is used for motor reversal.

In operation, the first push of pushbutton 851 causes both relays 962 and 964 to be energized through driver 956 and then kept latched on through relay contacts until one of the normally closed limit switches in series with the contact pair opens signaling a limit had been reached. In case of relay 962, shut down switch 866 will de-energize its coil. In the case of relay 964 it is forward limit switch 865 that de-energizes its coil to signal reversal of motor 852 or 902. When relay 962 is first energized, it provides motor voltage immediately. Relay 964 is simultaneously energized thereby supplying energizing voltage to the coil of reversing relay 966 which makes the motor turn so as to move forward. After the medicine vial is cut, limit switch 865 opens thereby de-energizing relay 964 which, in turn, turns off coil power to relay 966 causing motor to reverse and drive to the starting position at limit switch 866 causing system shutdown.

FIG. 45 shows the enlarged vertical storage chamber 1002 of embodiment 1000 using a standard medication capsule 600 which may be inserted with either end downward. A down tube 1018 supports breathing tube 520 and also guides medication below into the nebulizing chamber. A plunger housing 1006 with attached fixed finger rest guides plunger rod 1007 within with finger grip plate 1009 attached. This embodiment uses direct finger/hand actuation to release medication from capsule 600. Cap 1012 closes chamber 1002 using large diameter lock pin 1015 and small diameter lock pin 1016. The use of two different diameters makes it impossible to lock cap 1012 in a different orientation. As an aid to proper alignment, indicia 1013 and 1014 on cap and chamber respectively are used. Reference numeral 1004 is a funnel collection region for collection released medication and guiding it toward the nebulizing chamber.

FIG. 46 shows the inside of vertical storage chamber 1002. Base ring 1024 attaches chamber 1002 to funnel 1004 with central hole 1020. An extension 1025 is a bottom support for medication capsule 600 which end protrudes through slot 1026. By making 1026 longer, both types of medication capsule can be accommodated, narrow 600 type or wider 700 type. Vertical side cavity 1022 serves as an anvil support for the side of a medication capsule 600 or 700. A side view crossection of cap 1012 is shown in FIG. 47. It shows lock slots 1030 and 1031 to accept pins 1016 and 1015 respectively. Conical member 1035 is attached via leaf spring 1034 and is oriented so as to impinge on the top of the medication capsule when locked on, forcing it into the side recess 1022.

Figure 48:
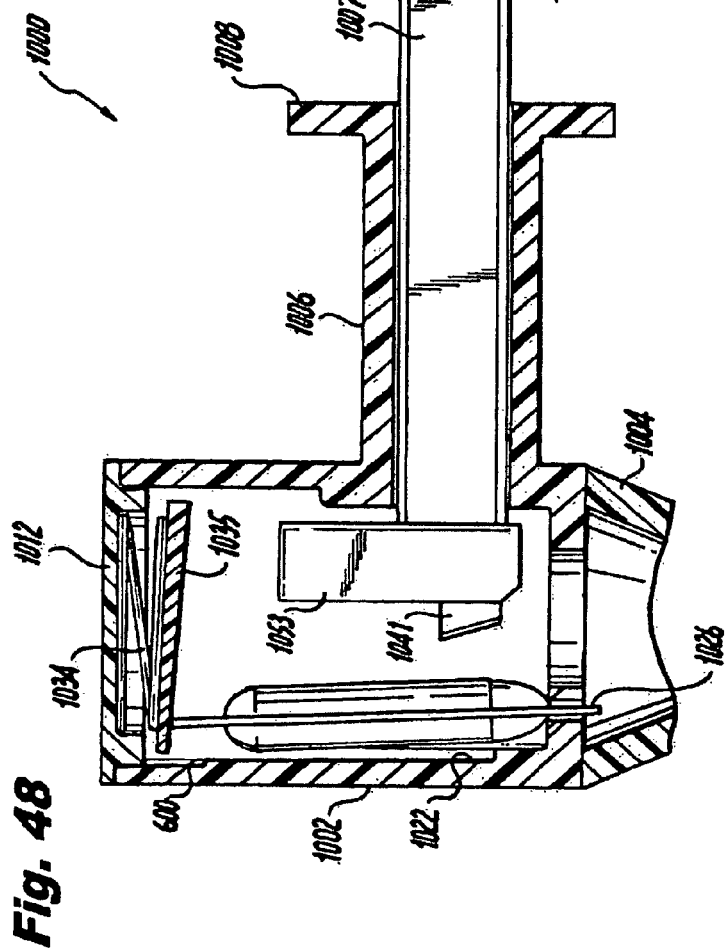
FIG. 48 is a side elevation of a vertical storage chamber assembly of an embodiment, in partial crossection, with a directly actuated vertical cutting blade located on a capsule crusher head.

FIG. 48 shows a side interior view of assembly 1000. Note that the distal end of plunger rod 1007 with blunt crusher head 1053 at its distal end, which receives a replaceable vertical blade 1041. Note also that capsule 600 is positioned at a slight angle within side anvil cavity 1022 by action of conical member 1035. When plunger rod 1007 is urged forward, blade 1041 will pierce capsule 600 at a low point and then the blunt end of blunt crusher head 1053 will impinge on the side of capsule 600, thereby opening the vertical slit caused by blade 1041, and thereby releasing medication.

While FIG. 48 shows a vertically oriented blade 1041, in alternate embodiments the blade can be oriented anywhere between a vertical and a horizontal orientation (such as shown in FIGS. 17-44).

Figure 48B:
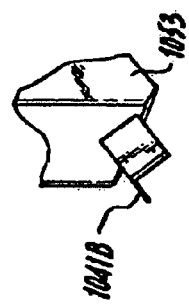
FIG. 48B is a close-up detail view of an alternate embodiment for an inverse V-shaped cutting blade located on a capsule crusher head.
Figure 48A:
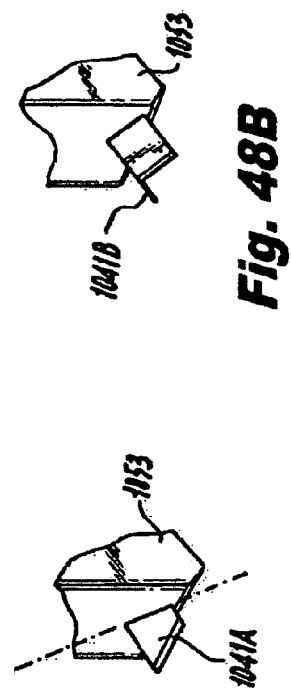
FIG. 48A is a close-up detail view of an alternate embodiment for an obliquely oriented cutting blade located on a capsule crusher head.

For example FIG. 48A shows a close-up detail view of an alternate embodiment for an obliquely oriented cutting blade located on a capsule crusher head.

FIG. 48B shows a close-up detail view of a further alternate embodiment for a multiple blade embodiment, such as, for example, an inverse V-shaped cutting blade located on a capsule crusher head. Other geometric configurations for multi-blade embodiments can be used.

Figure 49:
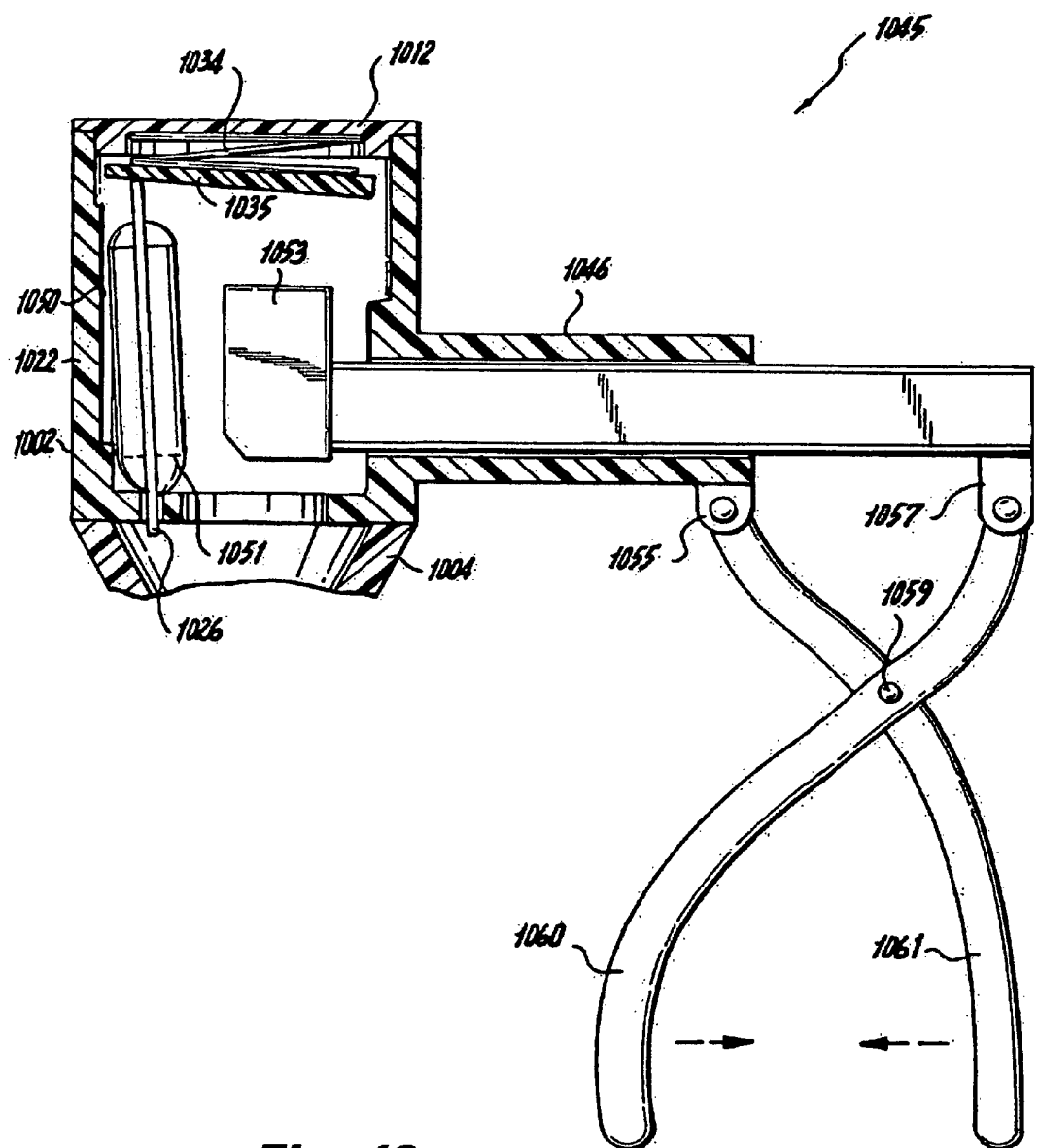
FIG. 49 is a side elevation of an alternate embodiment for a vertical storage chamber assembly of an embodiment, shown impartial crossection, with a crushing head and pliers grips for mechanical advantage.

FIG. 49 shows an alternate embodiment using capsule 1050 which has a weakened region 1051 adjacent its lower end as pushed into storage chamber 1002. In this embodiment, no blade is used. Instead, blunt crusher head 1053 is positioned to impact the side of capsule 1050 when plunger rod 1047 is urged forward within housing 1046. To offer mechanical advantage and permit whole hand operation, brackets 1055, 1057 and central pivot 1059 support pliers grips 1060 and 1061 to urge plunger rod 1047 forward. (This pliers assembly can also be used in any of the plunger embodiments, such as shown in FIG. 17, 25, 29, 34, 38 or 48 instead of direct actuation as shown.) As gas pressure rises within capsule 1050, the weakened area will burst, thereby releasing medication.

Since medication capsules 1050 can also be configured with the weakened area at the opposite end, FIGS. 50 and 51 contrast these two implementations showing capsule 1070 with a different weakened region 1071 at the end opposite to that in capsule 1050.

FIGS. 52-57 show a further alternate embodiment similar to that shown in FIG. 29, wherein a capsule follower 1172 is a U-shaped forwardly extending loop made of looped metal, such as a looped high grade, non-corrosive stainless steel rod. Capsule follower 1172 includes rearwardly extending prongs 1172b and 1172c joined by rounded distal end 1172a. Prongs 1172b and 1172c have ends imbedded within blade plunger 565. Capsule follower 1172 is positioned so that its curved end 1172a is positioned under the rear edge of cutting blade 570 of blade plunger 565, wherein blade 570 is angled, such as shown in FIG. 56, with respect to its contact with capsule 700 being held in place by capsule holder 710. As shown in FIG. 52 the position of curved end 1172a of capsule follower 1172 insures a smooth transfer of the severed capsule 700 to capsule follower 1172, which guides the severed capsule 700 out of the way of the fluid flow region 511 of capsule storage chamber 510 of FIG. 27.

Plunger guide 550 with handle 580 includes a upwardly extending wall, to which cap 590 is attached by threaded means, or other fastening means. Curved inside wall surface 1181 conforms to curved wall of the fluid flow region of blade plunger 565. Cap 590 is similar to that shown in FIGS. 29 and 30 with spring 750, spring retainer 760 and conical capsule holder 770 for capsule 700.

FIG. 52A is a close-up detail view of an alternate embodiment force cutting blade 570 with serrated edge 570a. The serrated edge 570a initiates the cutting without any initial billowing of the capsule, performing efficient opening of the capsule 700 to allow fluid flow therefrom.

In a previous embodiment (see FIGS. 3-5) a side storage chamber for use with a generally cylindrical medication cartridge having a distal pressure burstable seal was described. In one embodiment in FIGS. 3-5, the cylindrical cartridge may have a tapered front end with a pressure-burstable seal 43.

Figure 58:
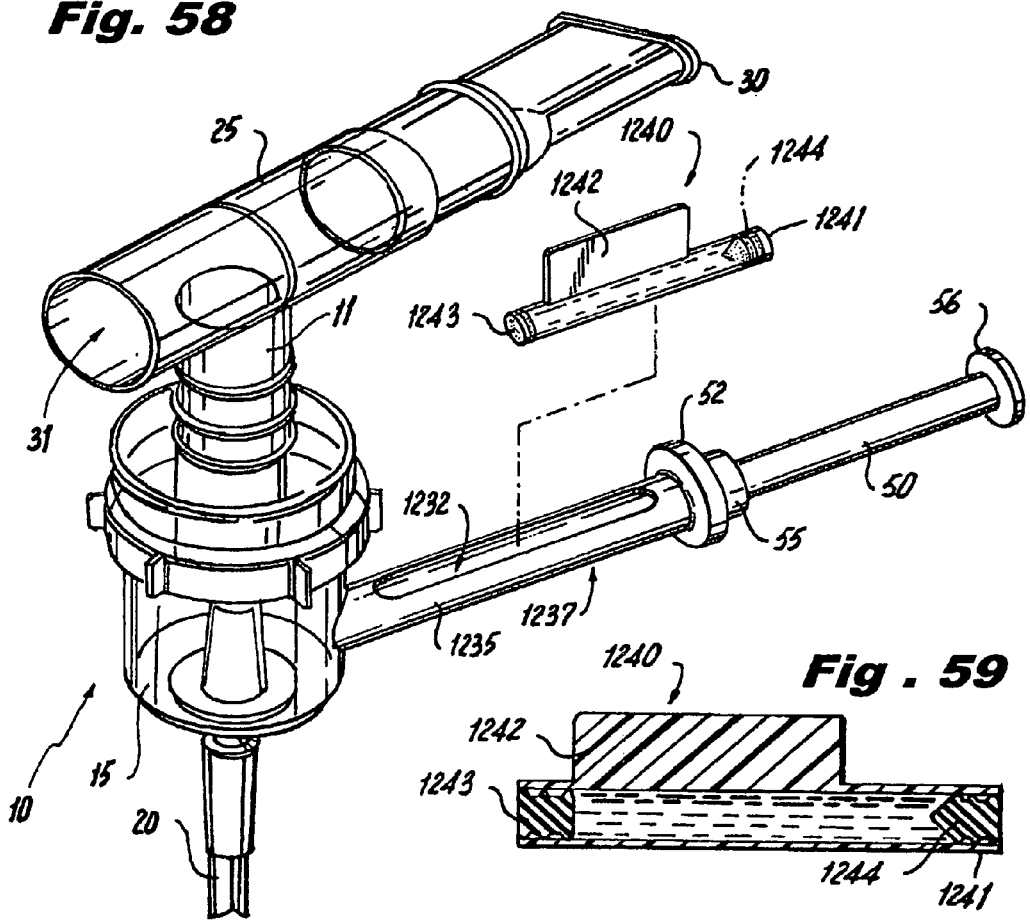
FIG. 58 is a perspective view of a nebulizer with side storage chamber using a medication dose cartridge with a uniform diameter and an elastomeric end seal.
Figure 59:
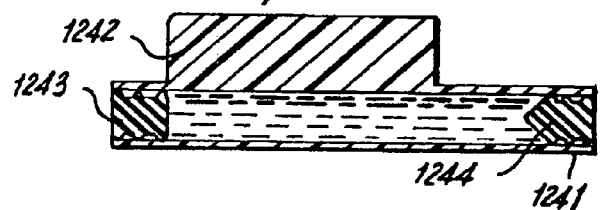
FIG. 59 is a side crossectional view of a medication dose cartridge having a uniform diameter and an elastomeric end seal.
Figure 60:
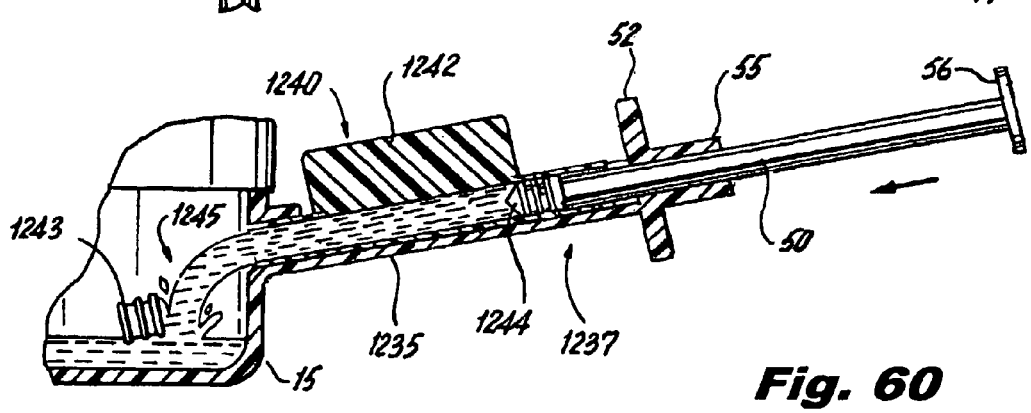
FIG. 60 is a side crossectional detail of the medication dose cartridge emptying into a nebulizing chamber.

In the present further embodiment of FIGS. 58-60, a similar arrangement using a medication cartridge 1240 is shown. The same type piston seal 1244 is at the outer end as in the previous embodiment. However, cartridge housing 1241 is of uniform diameter and is sealed at the inner end by an elastomeric seal 1243 thereby confining medication between the two seals. Handle and locator flange 1242 is a convenient grasping surface, and it also impinges on the front of storage chamber 1235 at the inner end to counteract piston rod 50 forces at the outer end. Substantially less force is needed to pressurize medication fluid to the point of overcoming friction force at front seal 1243 as compared to that which is required to burst a seal at a tapered end as in the previous embodiment.

FIG. 60 is a side view detail showing cartridge 1240 within cavity 1232 at a point just after inner seal 1243 is forced into the nebulizing chamber thereby spilling medication into the chamber.

FIGS. 61-63 describe the nebulizer cradle tower accessory which is used to insure foolproof setup and automatic starting of the compressor when the nebulizer is lifted off its cradle rest. This accessory is compatible with nebulizer type 1251 (see FIGS. 17-22) which uses a vertical storage chamber and cutter assembly as well as types 1252 which use a side storage chamber and piston rod as described in FIGS. 3-5 and 58-60.

FIG. 61 shows nebulizer cradle tower 1250 comprising base 1260, housing 1261, cradle 1265, "ready" indicator lamp 1266, compressor outlet 1267, emergency bypass switch 1268 and tower wall plug 1270. The objective is to be able to set up the nebulizer for immediate use with minimum fuss while in a stressful asthma attack scenario. The green indicator lamp 1266 only glows when the nebulizer is on the cradle if all of the prerequisite conditions are enabled. A medication cartridge is assumed to be pre-loaded in the storage chamber ready for discharge into the nebulizing chamber as the compressor automatically starts when the nebulizer is lifted off cradle 1265.

FIG. 62 shows the position of the relay 1281 which is energized by snap-action switch 1280 (the common and normally closed contacts are used) when cradle 1265 is lifted by counterweight 1276 whenever the nebulizer is lifted from the cradle; it pivots on pivot 1275. The weight of a nebulizer on cradle 1265 overcomes the counterweight force thereby opening cradle switch 1280 contacts. Note how nebulizer is cradled by mouthpiece 30 (or 230) and breather tube 25 (or 220) as shown in phantom lines in FIG. 61.

FIG. 62 also shows the location of the system on/off switch which is located at the back of tower housing 1261.

FIG. 63 is a wiring diagram of nebulizer cradle tower 1250. System on/off switch 1269 disables all electrical activity when in the off position; this is equivalent in action to unplugging the tower 1250 from the wall outlet. Switch 1269 is switched off to service the nebulizer, to clean it, or to reload another medicine cartridge; this keeps the compressor from switching on without the need to unplug. Switch 1269 must be turned to system on position to place tower 1250 in a ready mode. Note that indicator lamp 1266 (shown as a neon lamp with resistor) only glows if the cradle is weighted down by the nebulizer resting on it thereby interrupting current through relay 1281 coil and keeping normally open relay contacts 1285 open. Plug 1270 must be plugged into a powered outlet. Emergency switch 1268 must be in the open position; it is used only in case relay 1281 malfunctions. In addition, the lamp 1266 will only glow if compressor motor 410 is plugged into outlet 1267 and it switch 340a (on its housing) is in the ON position. Indicator lamp 1266 is a very low current indicator that is lighted by passing current through the compressor motor (when it is not running). An LED equivalent 110 VAC panel lamp such as a Philmore-Datak No. 11-105 can be substituted for the neon lamp/resistor shown. Indicator lamp 1266 goes OFF when nebulizer is lifted from cradle thereby operating relay and starting compressor motor 410.

FIGS. 64-66 illustrate the use of a medication cartridge 1340 of uniform diameter with a tail extension 1342 perpendicular to the length of the cartridge. This extension 1342 is designed to help insert cartridge 1340 through loading slot 1332 and then to retain cartridge 1340 within storage chamber 1335. Elastomeric edge beading 1338 at the tail end of loading slot 1332 of storage chamber 1335 must be slightly compressed during the loading operation; it then engages around the side edges of tail 1342. Cartridge push-out hole 1337 is used to remove a spent cartridge 1340.

Figures 67, 68:
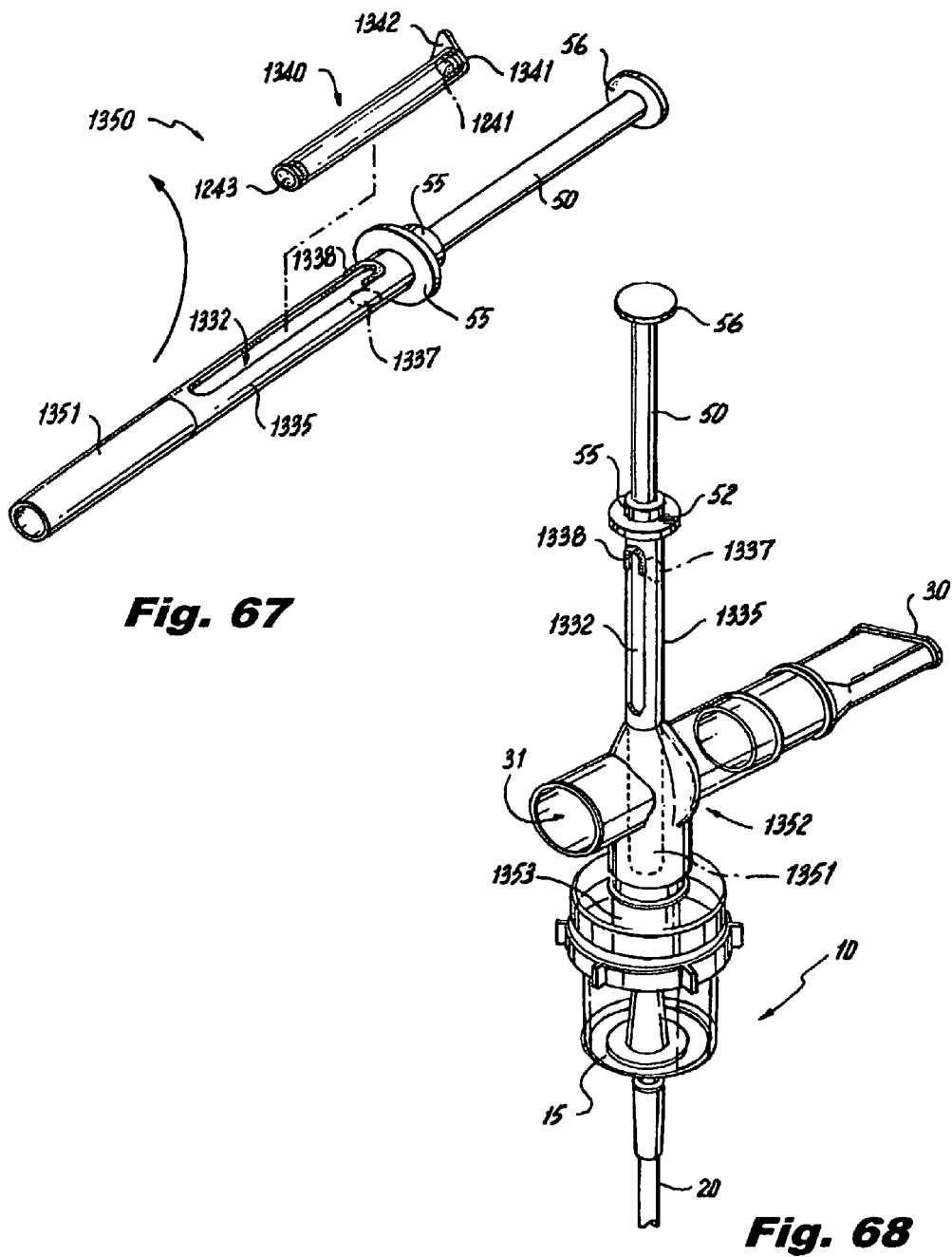
FIG. 67 is a perspective view of a modified storage chamber for vertical use.
FIG. 68 is a perspective view of a medication storage chamber mounted vertically atop a cross tube of a nebulizer.

FIG. 67 shows a modification 1350 of storage chamber 1335 for use in a vertical position over the nebulizing chamber as shown in FIG. 68. The modification consists of the addition of metal tube 1351, such as stainless steel or other compatible metal, attached at the nebulizer end. Extension tube 1351 is required to transverse cross tube 1352 to prevent actual liquid droplets from becoming entrained in the vapor flow and emerging through mouthpiece 30. Other modifications to the nebulizer include a bulge in the region where stainless steel tube 1351 passes through cross tube 1352, and an enlarged diameter down tube 1353; both of these modifications compensate for vapor flow restrictions introduced by the presence of tube 1351. The use of a conductive tube 1351 as opposed to a plastic is to help dissipate any static charge and to discourage the buildup of liquid droplets attached to the inner diameter surface.

FIGS. 69-72 illustrate the use of a simplified medication cartridge 1370 with uniform diameter and identical elastomeric seals 1371 at either end. The body of cartridge 1370 is a length of thick wall rigid plastic tubing. FIG. 70 is an enlarged side crossectional detail at the nebulizer end of cartridge 1370 within storage chamber 1375. Note that reduced diameter end ridge 1376 is used to prevent cartridge 1370 from passing through chamber 1375 while not presenting any impediment to seal 1371 from passing through when the cartridge is pressurized. Diameter "D" must be large enough to accommodate cartridge 1370. To relax the precision and tolerance required of diameter "D", the outside diameter of cartridge 1370, and the inside diameter of bottom ridge 1376, cartridge 1370 has a thick wall.

Although FIGS. 71 and 72 show a vertical storage chamber section 1375, cartridge 1370 and chamber 1375 can be used in any orientation. In FIG. 71, elastomeric bumps 1380 attached to the sides of loading slot 1377 are used as a cartridge retention mechanism since they must be slightly compressed to admit cartridge 1370.

Alternately, in FIG. 72, molded edge extensions 1381 forming spring members are used for the same purpose.

FIG. 73 shows cartridge 1370 in use on a sideways mounted storage chamber 1375.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

I claim:

1. A semi-automatic emergency medication dose nebulizer comprising:

a medication dosage capsule storage chamber embedded into and projecting outwardly from a nebulizer housing having a nebulizing chamber within said housing to receive liquid medication dosage;

said nebulizer chamber having an opening in a bottom of said housing to receive compressed air from a compressor for nebulizing said liquid medication dosage;

a horizontally extending breather above said nebulizer housing joined to said housing through a connecting tube extending vertically from said breather having a mouthpiece for use by a patient to receive said nebulized medication;

an apparatus for refilling said nebulizing chamber with medication;

said apparatus comprising said medication capsule storage chamber having an opening receiving a liquid medication dosage capsule containing a liquid medication;

wherein said capsule storage chamber includes a means for opening said medication capsule to release liquid medication from said liquid medication dosage capsule and into said nebulizing chamber thereby releasing all of the liquid medication within said cartridge at once into said nebulizing chamber;

said nebulizer further comprising a nebulizer cradle tower comprising a base, a housing and a cradle holding said nebulizer and an emergency bypass switch wherein the nebulizer is set up for immediate use by a user while in a stressful asthma attack;

wherein when the nebulizer is on said cradle and said liquid medication dosage capsule is pre-loaded in the storage chamber ready for discharge into the nebulizing chamber, said compressor automatically starts when said nebulizer is lifted off said cradle.

2. The semi-automatic emergency medication dose nebulizer as in claim 1 further comprising a relay energized by said cradle switch when said nebulizer is lifted from said cradle; wherein the weight of said nebulizer on said cradle overcomes a counterweight force, thereby opening a respective contact on said cradle switch;

said cradle tower having a system on/off switch; said on/off switch disabling all electrical activity when in the off position;

said on/off switch being turned to a system on position to place said cradle tower in a ready mode, said cradle tower further having an indicator lamp which only glows if said cradle is weighted down by said nebulizer resting on said cradle, thereby interrupting current through said relay and keeping respective normally open relay contacts open;

wherein further said indicator lamp goes to an off position when said nebulizer is lifted from said cradle, thereby operating said relay and starting said compressor.

3. The semi-automatic emergency medication dose nebulizer as in claim 1 wherein said means for opening said medication capsule to release liquid medication from said liquid medication dosage capsule and into said nebulizing chamber thereby releasing all of the liquid medication within said cartridge at once into said nebulizing chamber comprises:

said capsule storage chamber having a pair of opposite ends, one of said ends being an inner nebulizer end fixed communicating with said nebulizing chamber and wherein said opposite end is an outer end, said capsule storage chamber projecting radially outward from said nebulizing chamber within said nebulizer housing so that an outer end of said capsule storage chamber is accessible to a user;

said medication dosage capsule having an inner end having a pressure-burstable seal, said inner end being nested near said inner end of said capsule storage chamber when said medication capsule is within said capsule storage chamber;

wherein said outer end of said capsule storage chamber includes a means for applying pressure to said medication within said medication dosage capsule to cause said seal to be dislodged out of the inner end of said cartridge and into said nebulizing chamber thereby releasing all of the medication within said cartridge at once into said nebulizing chamber.

4. The semi-automatic emergency medication dose nebulizer as in claim 1 wherein said means for opening said medication capsule to release liquid medication from said liquid medication dosage capsule and into said nebulizing chamber thereby releasing all of the liquid medication within said cartridge at once into said nebulizing chamber comprises:

said capsule storage chamber comprising a recharging tube containing a capsule storage chamber aligned with said connecting tube for receiving a vertically oriented medication dosage capsule containing a liquid medication; and, a horizontally extending cutting blade for completely severing said vertically oriented liquid medication dosage capsule by slicing through a side of said capsule causing removal and relocation of a lower portion of said capsule; said blade having a follower paddle mounted behind said horizontally oriented blade to push a severed portion of said vertically oriented capsule out of the line of flow of said medication, allowing liquid medication to flow downward when released from said capsule, to flow under the influence of gravity into said nebulizing chamber.

* * * * *